(12) United States Patent
Gorshkov et al.

(10) Patent No.: US 10,007,885 B1
(45) Date of Patent: Jun. 26, 2018

(54) DETERMINING A MODAL AMPLITUDE OF AN INHOMOGENEOUS FIELD WITH A QUANTUM SENSOR

(71) Applicant: The United States of America, as Represented by the Secretary of Commerce, Washington, DC (US)

(72) Inventors: Alexey V. Gorshkov, Rockville, MD (US); Michael S. Foss-Feig, Baltimore, MD (US); Zachary Eldredge, Adelphi, MD (US); Steven L. Rolston, Derwood, MD (US)

(73) Assignee: THE UNITED STATES OF AMERCA, AS REPRESENTED BY THE SECRETARY OF COMMERCE, Washington, DC (US)

( * ) Notice: Subject to any disclaimer, the term of this patent is extended or adjusted under 35 U.S.C. 154(b) by 0 days. days.

(21) Appl. No.: 15/650,216

(22) Filed: Jul. 14, 2017

(51) Int. Cl.
| | |
|---|---|
| *H01L 29/06* | (2006.01) |
| *G06N 99/00* | (2010.01) |
| *G01N 24/00* | (2006.01) |
| *G01N 35/00* | (2006.01) |
| *H04B 10/70* | (2013.01) |
| *G01N 29/44* | (2006.01) |
| *G06F 17/10* | (2006.01) |

(52) U.S. Cl.
CPC ......... *G06N 99/002* (2013.01); *G01N 24/008* (2013.01); *G01N 29/4472* (2013.01); *G01N 35/0098* (2013.01); *G06F 17/10* (2013.01); *H04B 10/70* (2013.01)

(58) Field of Classification Search
CPC ............... G06N 99/002; G01N 24/008; G01N 29/4472; G01N 35/0098; G06F 17/10; H04B 10/70

USPC ........................................................... 257/31
See application file for complete search history.

(56) References Cited

U.S. PATENT DOCUMENTS

| | | | |
|---|---|---|---|
| 6,675,154 B2 * | 1/2004 | Jaeger .................... | B82Y 10/00 706/4 |
| 7,483,142 B2 * | 1/2009 | Kent ...................... | H04B 10/70 356/450 |

(Continued)

OTHER PUBLICATIONS

J.J Bollinger, et al., Optimal frequency measurements with maximally correlated states, Physical Review A, 1996, R464-R4652, 54(6).

(Continued)

*Primary Examiner* — Tu-Tu Ho
(74) *Attorney, Agent, or Firm* — Toby D. Hain

(57) ABSTRACT

Determining a modal amplitude of an inhomogeneous field includes: preparing an initial entangled state of a quantum sensor; subjecting the quantum sensor to the inhomogeneous field of the analyte; subjecting a first qudit sensor of the quantum sensor to a first perturbation pulse; receiving the first perturbation pulse by the first qudit sensor to prepare a first intermediate entangled state of the quantum sensor, the first intermediate entangled state comprising a first intermediate linear superposition; changing the initial linear superposition to the first intermediate linear superposition in response to receiving the first perturbation pulse by the quantum sensor; and determining a final entangled state of the quantum sensor after applying the first perturbation pulse to determine the modal amplitude of the inhomogeneous field of the analyte.

18 Claims, 20 Drawing Sheets

(56) References Cited

U.S. PATENT DOCUMENTS 8,547,090 B2    10/2013  Lukin et al.
8,947,080 B2    2/2015   Lukin et al.
9,329,152 B2 *  5/2016   Walker .................. G01R 33/02

OTHER PUBLICATIONS

R. Dolde, et al., Room-temperature entanglement between single defect spins in diamond, Nature Physics, 2013, 139-143, 9.
P. Komar, et al., A quantum network of clocks, Nature Physics, 2014, 582-587, 10.
Eugene S. Polzik, et al., Entanglement and spin squeezing in a network of distant optical lattice clocks, Physical Review A, 2016, 021401-1-021404-5, 93.
D.J. Wineland, et at., Spin squeezing and reduced quantum noise in spectroscopy, Physical Review A, 1992, R6797-R6800, 46(11).

* cited by examiner (A)
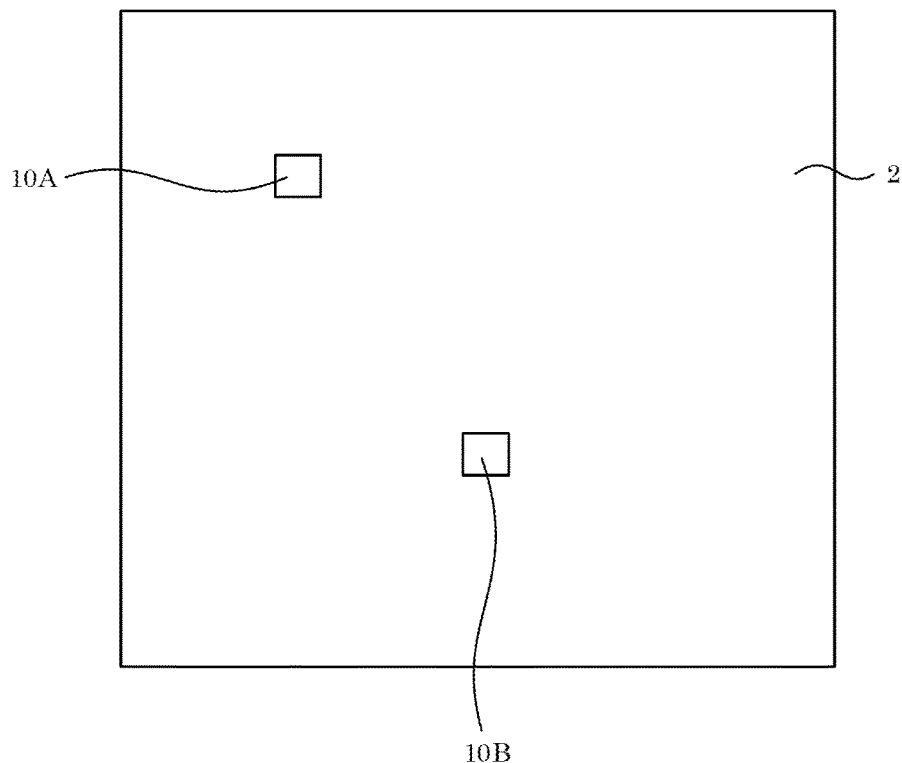
(B)
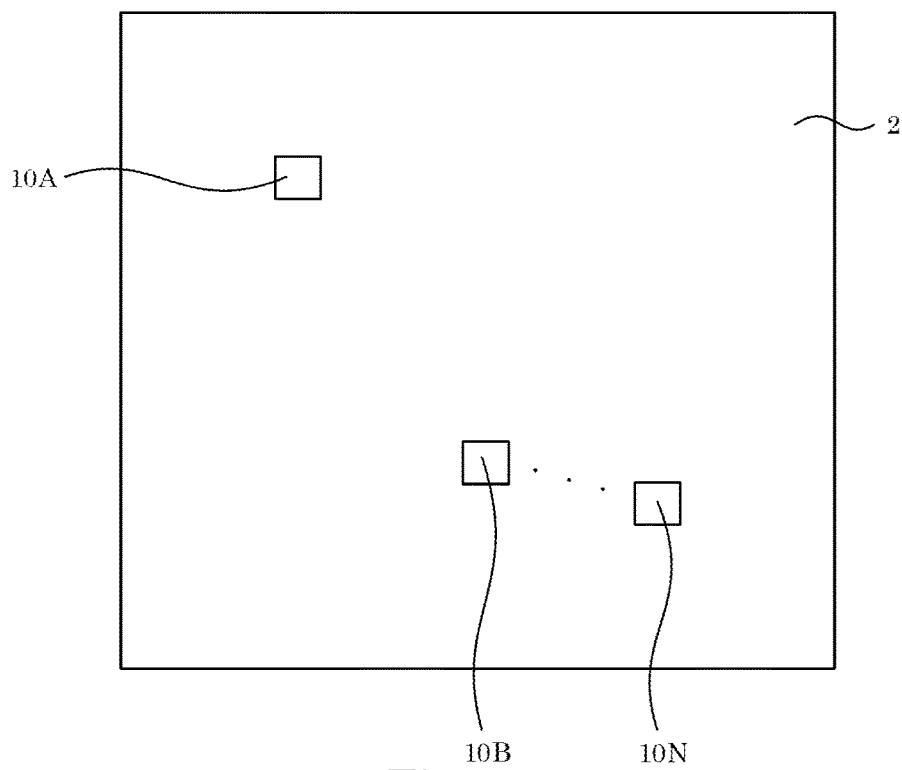
Figure 2

Initial entangled state: $\frac{1}{\sqrt{2}}\left[|000\rangle + |111\rangle\right]$ State evolved for time t1 under coupling to inhomogeneous field:

$\frac{1}{\sqrt{2}}\left[|000\rangle + e^{-it1(\theta1+\theta2+\theta3)}|111\rangle\right]$ First terminating pulse at $t1 = \alpha_1 t_f$ Intermediate entangled state: $\frac{1}{\sqrt{2}}\left[|000\rangle + e^{-it1(\theta1+\theta2+\theta3)}|211\rangle\right]$ Entangled state evolved for time t2-t1 under coupling to inhomogeneous field:

$\frac{1}{\sqrt{2}}\left[|000\rangle + e^{-it1(\theta1+\theta2+\theta3)-i(t2-t1)(\theta2+\theta3)}|211\rangle\right]$ Second terminating pulse at $t2 = \alpha_2 t_f$ Final entangled state:

$\frac{1}{\sqrt{2}}\left[|000\rangle + e^{-it1(\theta1+\theta2+\theta3)-i(t2-t1)(\theta2+\theta3)}|221\rangle\right]$ Entangled state evolved for time tf-t2 under coupling to inhomogeneous field:

$\frac{1}{\sqrt{2}}\left[|000\rangle + e^{-iqt_f}|221\rangle\right]$

Figure 10

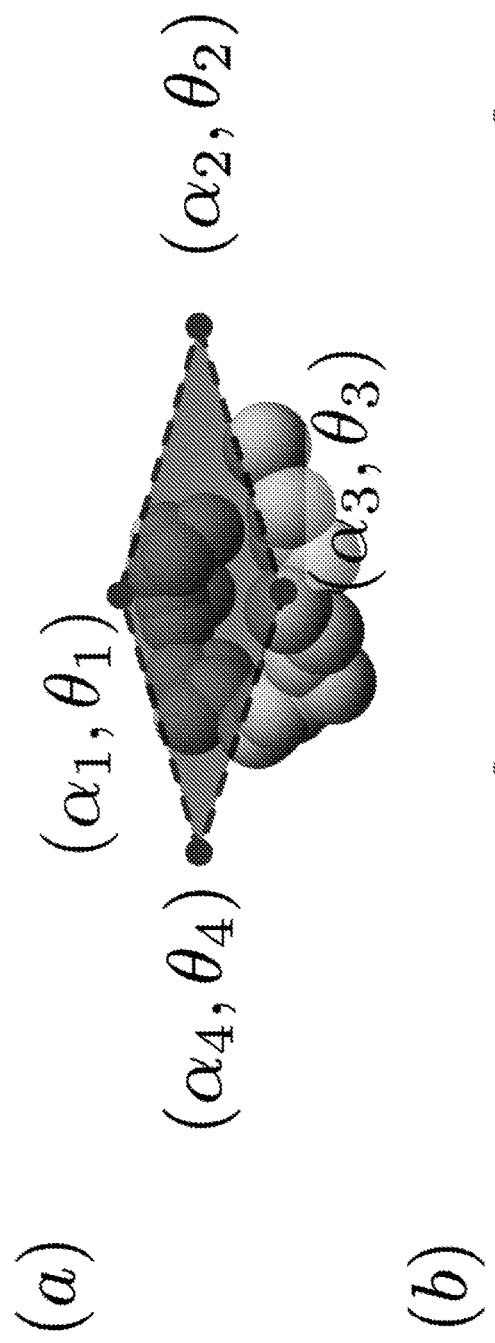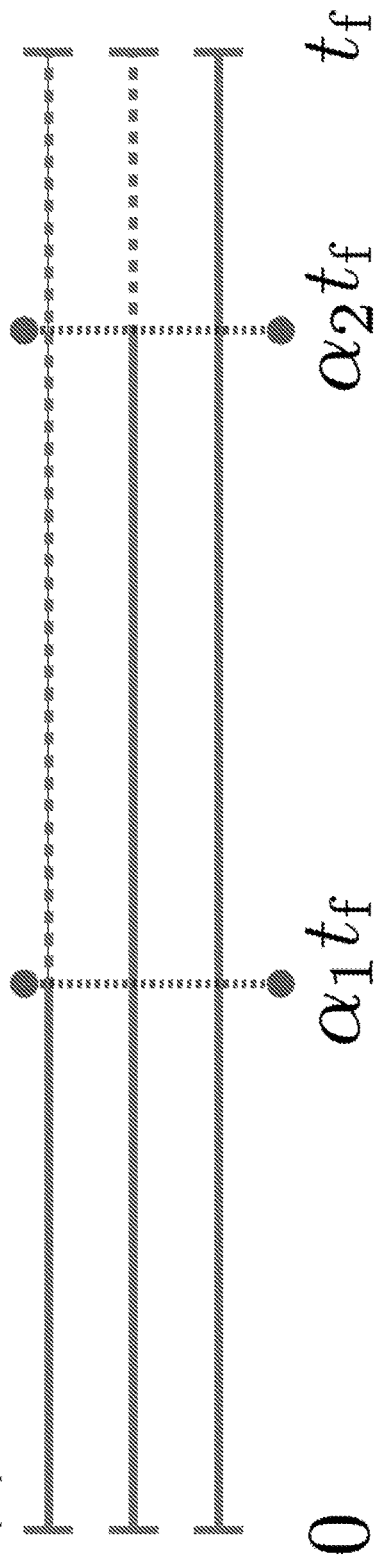
Figure 16

US 10,007,885 B1

DETERMINING A MODAL AMPLITUDE OF AN INHOMOGENEOUS FIELD WITH A QUANTUM SENSOR

STATEMENT REGARDING FEDERALLY SPONSORED RESEARCH

This invention was made with United States Government support from the National Institute of Standards and Technology, an agency of the United States Department of Commerce. The Government has certain rights in the invention.

BRIEF DESCRIPTION

Disclosed is a process for determining a modal amplitude of an inhomogeneous field of an analyte, the process comprising: preparing an initial entangled state of a quantum sensor, the initial entangled state comprising: a first quantum level; a second quantum level; and an energy difference between the second quantum level and the first quantum level, the energy difference being linearly dependent on a strength of the inhomogeneous field, the initial entangled state being an initial linear superposition of the first quantum level and the second quantum level, and the quantum sensor comprising a plurality of qudit sensors; subjecting the quantum sensor to the inhomogeneous field of the analyte; subjecting a first qudit sensor of the quantum sensor to a first perturbation pulse; receiving the first perturbation pulse by the first qudit sensor to prepare a first intermediate entangled state of the quantum sensor, the first intermediate entangled state comprising a first intermediate linear superposition; changing the initial linear superposition to the first intermediate linear superposition in response to receiving the first perturbation pulse by the quantum sensor; and determining a final entangled state of the quantum sensor after applying the first perturbation pulse to determine the modal amplitude of the inhomogeneous field of the analyte.

BRIEF DESCRIPTION OF THE DRAWINGS

The following descriptions should not be considered limiting in any way. With reference to the accompanying drawings, like elements are numbered alike.

FIG. 2 shows a quantum sensor;

FIG. 10 shows a change from an initial entangled state to a final entangled state through an intermediate entangled state in response to subjecting a quantum sensor to a plurality of terminating pulses;

FIG. 16 shows an analyte that includes a molecule disposed proximate to a quantum sensor in panel A, and panel B shows a time over which the quantum sensor is subjected to a plurality of terminating pulses;

DETAILED DESCRIPTION

A detailed description of one or more embodiments is presented herein by way of exemplification and not limitation.

It has been discovered that a process for measuring a modal amplitude of an inhomogeneous field of an analyte with a quantum sensor provides a determination of a spatial variation of the inhomogeneous field. Advantageously, the process can be used in gravimetry, spectroscopy, rotation sensing, and the like. Moreover, the process can be used in any setting where Ramsey spectroscopy can be applied if a quantity of interest is nonlocal.

Figure 1:
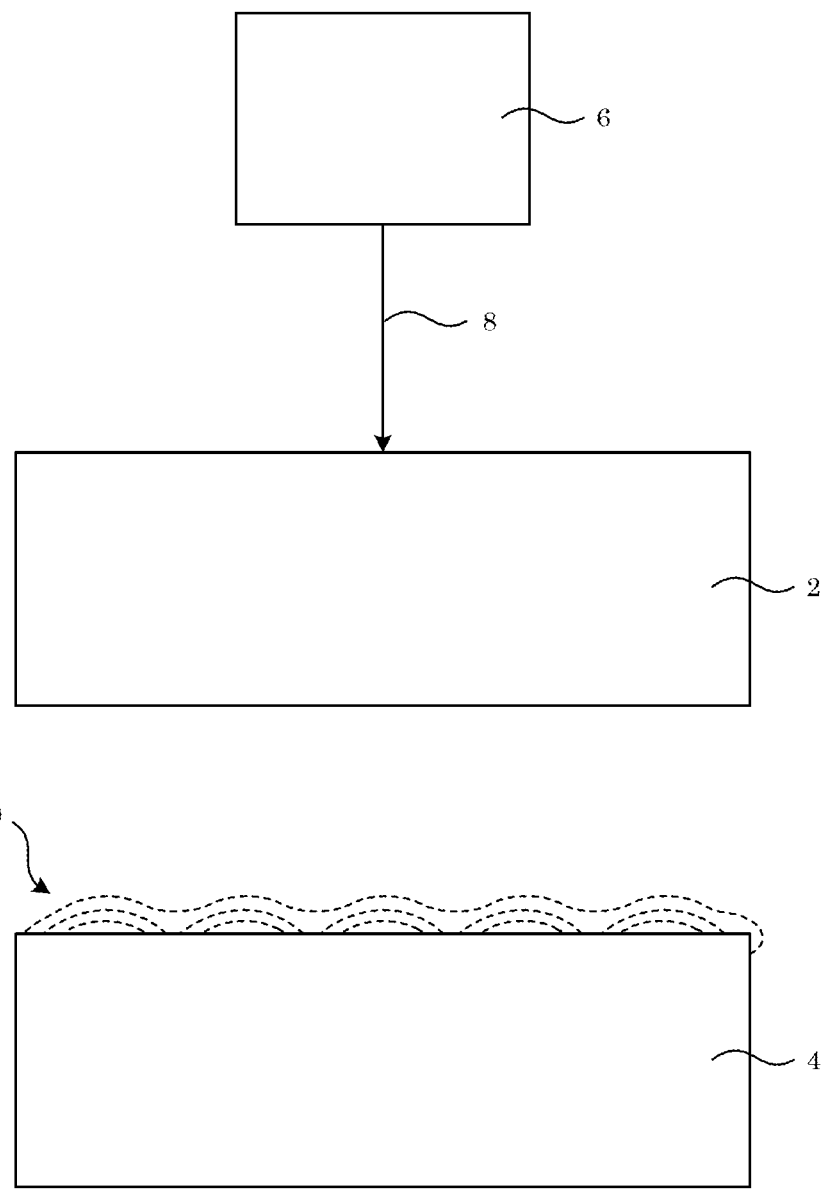
FIG. 1 shows a system for determining a modal amplitude of an inhomogeneous field of an analyte.

In an embodiment, with reference to FIG. 1, system 100 includes quantum sensor 2 disposed proximate to analyte 4 such that quantum sensor 2 is subjected to inhomogeneous field 50 of analyte 4. Additionally, system 100 includes pulse source 6 that provides perturbation pulse 8 to quantum sensor 2. Quantum sensor 2 determines a modal amplitude of inhomogeneous field 50 of analyte 4 in response to receipt of perturbation pulse 8.

In an embodiment, as shown in panel A of FIG. 2, quantum sensor 2 includes a plurality of qudit sensors, e.g., first qudit sensor 10A and second qudit sensor 10B. It is contemplated that quantum sensor 2 can include an arbitrary number N of qudit sensors as shown in panel B of FIG. 2.

Figure 3:
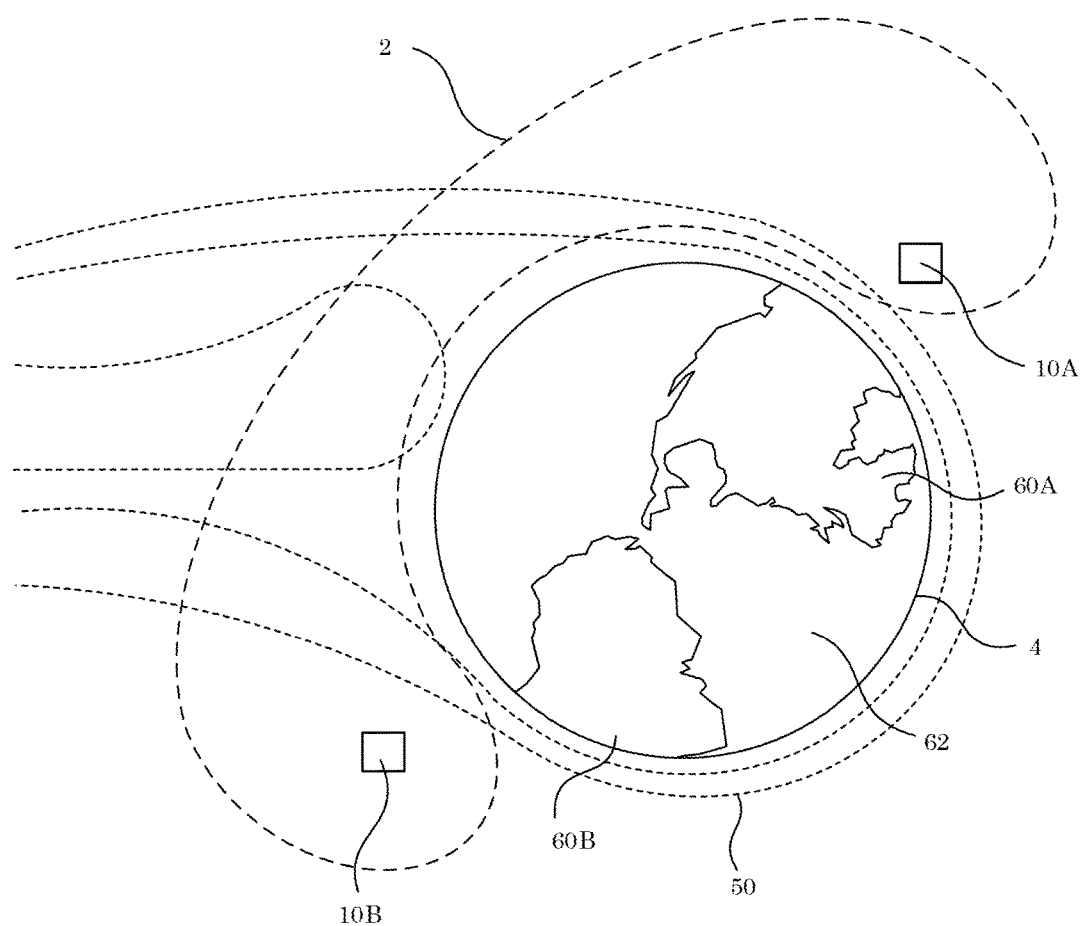
FIG. 3 shows a system for determining a modal amplitude of an inhomogeneous field of an analyte.

In a particular embodiment, with reference to FIG. 3, analyte 4 can be planet 62 that includes a plurality of continents 60 (e.g., first continent 60A, second continent 60B), wherein planet 62 has inhomogeneous field 50, e.g., an inhomogeneous magnetosphere. Quantum sensor 2 is disposed proximate to planet 62 in a presence of inhomogeneous field 50 such that qudits 10 (e.g., 10A, 10B) are subjected to inhomogeneous field 50, here the inhomogeneous magnetosphere. Further, pulse source 6 (not shown) provides pulse 8 (not shown) to qudits (10A, 10B). As a result, quantum sensor 2 determines the modal amplitude of inhomogeneous field 50 of planet 62.

Figure 4:
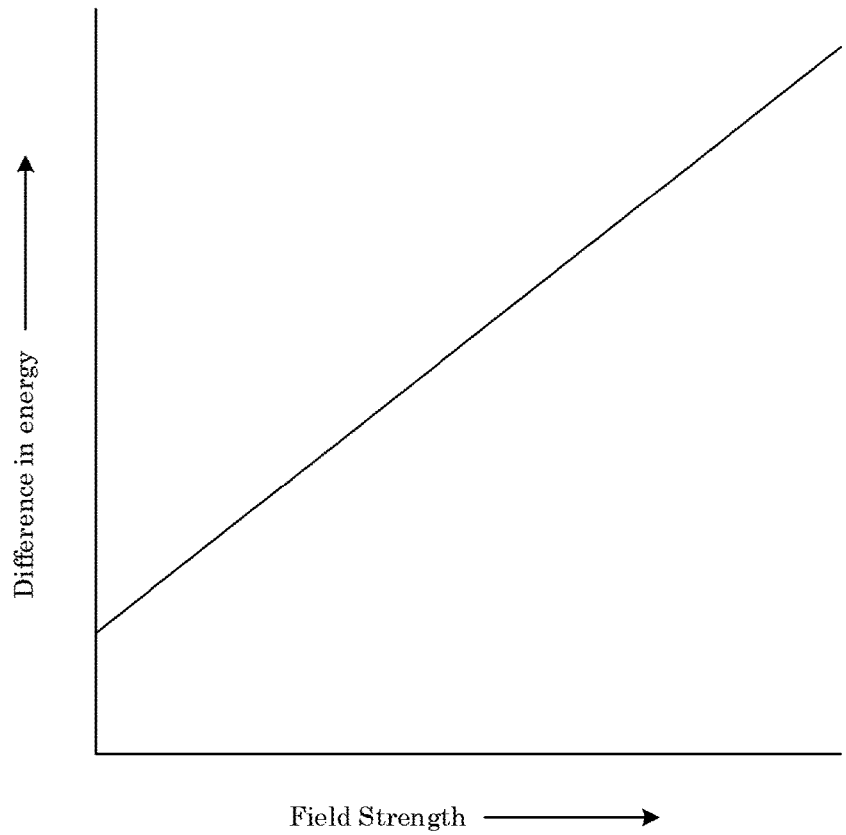
FIG. 4 shows a graph of difference in energy versus field strength.

In quantum sensor 2, first qudit sensor 10A includes a plurality of quantum levels that are subject to entanglement with a plurality of quantum levels of second qudit sensor 10B to provide an initial entangled state of quantum sensor 2. The initial entangled state includes a first quantum level, a second quantum level, and an energy difference between the second quantum level and the first quantum level. Here, the energy difference between the first quantum level and the second quantum level of the initial entangled state is linearly dependent on a strength of inhomogeneous field 50 as shown in FIG. 4. Moreover, the initial entangled state is an initial linear superposition of the first quantum level and the second quantum level.

Qudit 10 can be a two-level quantum system such as provided by qubits, a three-level quantum system such as provided by qutrits, a four-level quantum system, . . . , an m-level quantum system, and the like, wherein m is an integer. Accordingly, qudits 10 can include a qubit, qutrit, a quartit, and the like, or a combination of such qudits. Exemplary qubits include a nuclear spin-1/2, an electronic spin-1/2, or any two chosen levels of a neutral atom, an ion, a molecule, a solid-state defect, a superconducting circuit, and the like. Exemplary qutrits include a spin-1 particle or any three chosen levels of a neutral atom, an ion, a molecule, a solid-state defect, a superconducting circuit, and the like. In an embodiment, qudits 10 include a neutral atom, an ion, a molecule, a solid-state defect (such as a nitrogen vacancy color center in diamond), a superconducting circuit, and the like, or a combination.

In an embodiment, first qudit sensor 10A is a qubit, and second qudit sensor 10B is a qubit. In an embodiment, first qudit sensor 10A is a qutrit, and second qudit sensor 10B is a qutrit. In an embodiment, first qudit sensor 10A is a qubit, and second qudit sensor 10B is a qutrit.

It is contemplated that qudit sensors 10 can be included in quantum sensor 2 as a monolithic device, wherein quantum sensor 2 can include the substrate in which qudit sensors 10 are disposed and arranged. Here, qudit sensors 10 are in mechanical communication via phonons in the substrate or interact via electric or magnetic interactions. Qudit sensors 10 alternatively can be arranged in a network such that the plurality of qudit sensors 10 are subject to quantum entanglement using flying photonic qubits.

It is contemplated that the initial entangled state of quantum sensor 2 can be changed to an intermediate entangled state or final entangled state in response to receipt of perturbation pulse 8 by quantum sensor 2. In an embodiment, qudits 10 include first qutrit 10A and second qutrit 10B, wherein the initial entangled state is the first linear superposition $$\frac{1}{\sqrt{2}}[|00\rangle + |11\rangle],$$

which then evolves under the coupling to the inhomogeneous field to $$\frac{1}{\sqrt{2}}[|00\rangle + e^{-i\vartheta_1}|11\rangle]$$

for some phase $\vartheta_1$ and the final entangled state is final linear superposition $$\frac{1}{\sqrt{2}}[|00\rangle + e^{-i\vartheta_1}|21\rangle]$$

which then also evolves under the coupling to the inhomogeneous field to $$\frac{1}{\sqrt{2}}[|00\rangle + e^{-it_f q}|11\rangle].$$

Here, ket $|00\rangle$ refers to both qutrits in state $|0\rangle$; ket $|11\rangle$ refers to both qutrits in state $|0\rangle$; ket $|21\rangle$ refers to the first qutrit in state $|2\rangle$ and the second qutrit in state $|1\rangle$; tf is the total evolution time and q is the modal amplitude that is being measured.

According to an embodiment, qudits 10 include first qubit 10A and second qubit 10B, wherein the initial entangled state is an initial linear superposition $$\frac{1}{\sqrt{2}}[|000\rangle + |111\rangle].$$

The intermediate entangled state includes intermediate linear superposition $$\frac{1}{\sqrt{2}}[|100\rangle + e^{-i\vartheta_2}|011\rangle]$$

for some phase $\vartheta_2$ picked up due to coupling to the inhomogeneous field. The final entangled state includes final linear superposition $$\frac{1}{\sqrt{2}}[|110\rangle + e^{-it_f q}|001\rangle].$$

Quantum sensor 2 is subjected to inhomogeneous field 50 of analyte 4. Exemplary analytes include a planet, an organism (e.g., a human) an organ (e.g., a brain, heart, and the like), a tissue (e.g., cardiac tissue), a molecule (e.g., including a macromolecule such as a protein or nucleic acid), an atom, and the like.

Inhomogeneous field 50 of analyte 4 includes modal amplitude q that is determined by quantum sensor 2 in response to receipt of perturbation pulse 8 by quantum sensor 2 from pulse source 6. Exemplary inhomogeneous fields 50 include an electric field, magnetic field, temperature, gravitational field, strain, and the like, or a combination thereof.

Pulse source 6 provides perturbation pulse 8 to quantum sensor 2. Perturbation pulse 8 can be electromagnetic radiation having a frequency near resonance with the qudit, such as, for example, optical frequencies for optical qubits, microwave frequencies for microwave qubits, or radiofrequencies for radiofrequency qubits. A duration of perturbation pulse 8 is short enough so that inhomogeneous field 50 has negligible effect on qudit 10 during perturbation pulse 8. Perturbation pulse 8 produced by pulse source 6 is received by an individual qudit sensor (e.g., 10A, 10B, ..., 10N). In response to receipt of perturbation pulse 8 by qudit sensor 10 (e.g., 10A, 10B), the first entangled state is changed to an intermediate entangled state or final entangled state of quantum sensor 2.

Exemplary pulse sources 6 include a laser, a microwave source, a radiofrequency source, or a combination thereof.

Quantum Sensor 2 can be made in various ways. In an embodiment, a process for making quantum sensor 2 includes disposing a first qudit sensor 10A at a first position relative to analyte 4 and disposing second qudit sensor 10B at a second position relative to analyte 4 and first qudit sensor 10A. According to an embodiment, a process for making quantum sensor 2 includes providing a substrate; disposing first qudit sensor 10A in the substrate; and disposing second qudit sensor 10B in the substrate at a selected position relative to first qudit sensor 10A.

Quantum sensor 2 has numerous beneficial uses, including determining modal amplitude q of inhomogeneous field 50 of analyte 4. In an embodiment, a process for determining modal amplitude q of inhomogeneous field 50 of analyte 4 includes: preparing an initial entangled state of quantum sensor 2, the initial entangled state including: a first quantum level; a second quantum level; and an energy difference between the second quantum level and the first quantum level, the energy difference being linearly dependent on a strength of inhomogeneous field 50, the initial entangled state being an initial linear superposition of the first quantum level and the second quantum level, and quantum sensor 2 including a plurality of qudit sensors 10; subjecting quantum sensor 2 to inhomogeneous field 50 of analyte 4; subjecting first qudit sensor 10A of quantum sensor 10 to a first perturbation pulse; receiving the first perturbation pulse by first qudit sensor 10A to prepare a first intermediate entangled state of quantum sensor 2, the first intermediate entangled state comprising a first intermediate linear superposition; changing the initial linear superposition to the first intermediate linear superposition in response to receiving the first perturbation pulse by quantum sensor 2; and determining a final entangled state of quantum sensor 2 after applying the first perturbation pulse to determine modal amplitude q of inhomogeneous field 50 of analyte 4.

In the process, preparing an initial entangled state of quantum sensor 2 includes preparing a pure unentangled (i.e., product) state of the qudit sensors. It is contemplated that preparing the initial entangled state of the quantum sensor includes subjecting the qudits to direct entangling interaction among the qudits. Here, the interaction could be, for example, electromagnetic interaction such as electric or magnetic dipole-dipole interaction or a van der Waals interaction. In an aspect, use of interactions between two of the qudits can prepare an entangled state shared between them, and then an interaction between a third qudit and one of the first two qudits can be used to add the third qudit to the entangled state, then a fourth qudit, and the like. Preparing the initial entangled state of the quantum sensor also can include subjecting the qudits to a mediator comprising a photon, a phonon, or a combination thereof. Here, one can entangle a given qudit with a mediator and then send the mediator to the second qudit. Alternatively, one can entangle two qudits with their own mediators and then send the mediators towards each other for a joint measurement. One can then repeat this process to add additional qudits to the entangled state.

In the process, subjecting quantum sensor 2 to inhomogeneous field 50 of analyte 4 includes placing qudit sensors at positions where the knowledge of the inhomogeneous field of interest is needed.

In the process, subjecting first qudit sensor 10A of quantum sensor 10 to a first perturbation pulse includes applying to the qudit sensor a short near-resonant pulse of electromagnetic radiation that has just the right pulse area (equal to n) to transfer the qudit state from $|1\rangle$ to $|2\rangle$ for the case of a terminating pulse or to swap qudit levels $|1\rangle$ and $|2\rangle$ for the case of an echo pulse.

In the process, receiving the first perturbation pulse by first qudit sensor 10A to prepare a first intermediate entangled state of quantum sensor 2 includes transferring the qudit state from $|1\rangle$ to $|2\rangle$ for the case of a terminating pulse or swapping qudit levels $|1\rangle$ and $|2\rangle$ for the case of an echo pulse.

In the process, changing the initial linear superposition to the first intermediate linear superposition in response to receiving the first perturbation pulse by quantum sensor 2 includes transferring the qudit state from $|1\rangle$ to $|2\rangle$ for the case of a terminating pulse or swapping qudit levels $|1\rangle$ and $|2\rangle$ for the case of an echo pulse.

In the process, determining a final entangled state of quantum sensor 2 after applying the first perturbation pulse and after waiting for the final time includes undoing all termination and echo pulses and then projectively measuring each qudit in the $$\frac{1}{\sqrt{2}}[|0\rangle \pm |1\rangle]$$

basis and then multiplying the answers (plus or minus one) to compute the parity P, whose quantum mechanical expectation value depends on modal amplitude q as $\langle P \rangle = \cos(q\, tf)$. One can then extract q by repeating the experiment many times. Here, modal amplitude q includes a linear combination of a plurality of mode components $\alpha_i$ of a mode A and a plurality of energy components $\theta i$ as $$q = \sum_i^N \alpha_i \theta_i,$$

wherein N is a total number of qudits 10, and i is an integer from 1 to N.

Figure 5:
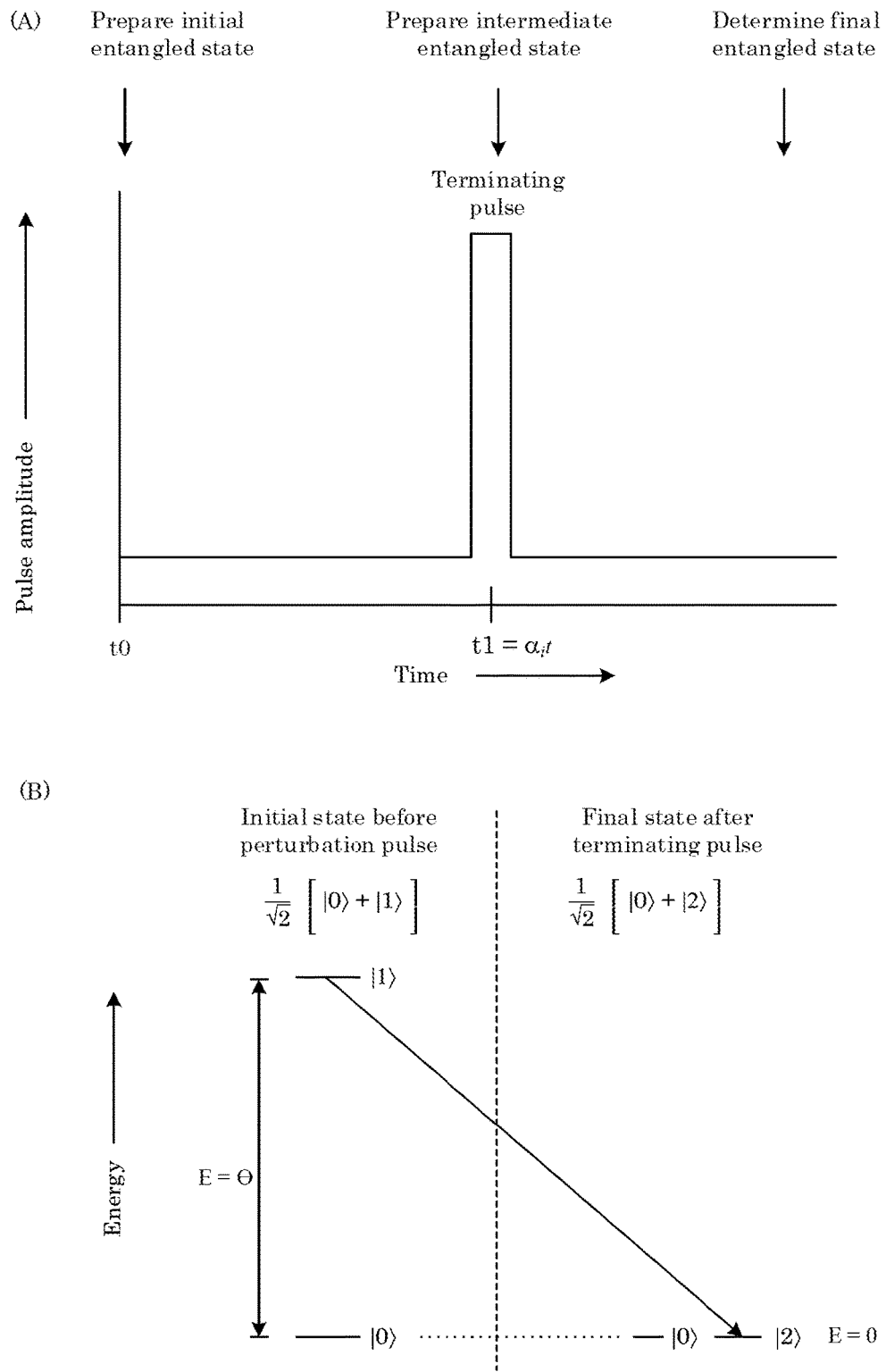
FIG. 5 shows a graph of amplitude of a versus time in panel A, and panel B shows a change from an initial entangled state to a final entangled state in response to subjecting a quantum sensor to a terminating pulse.
Figure 7:
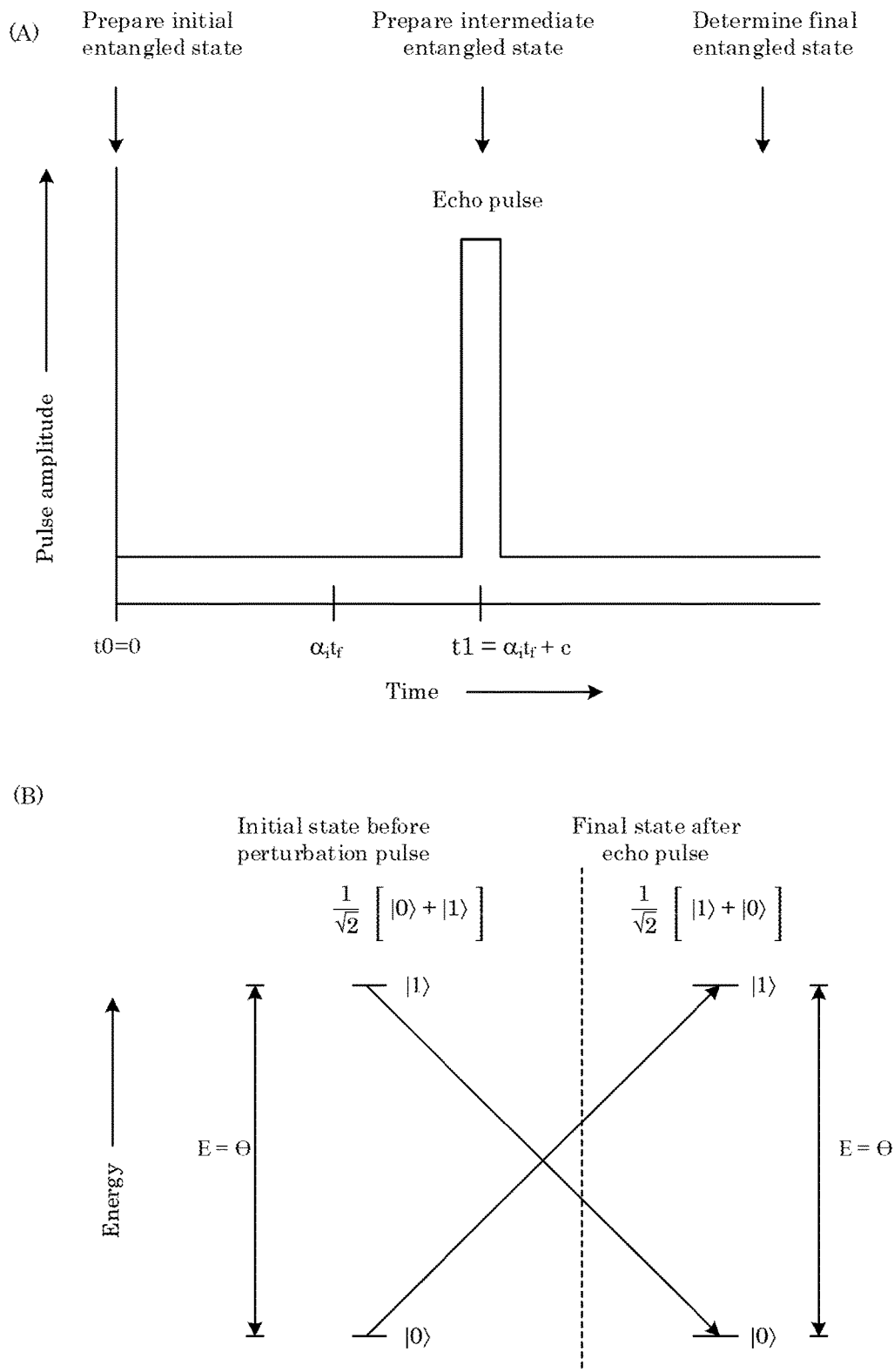
FIG. 7 shows a graph of amplitude of an echo pulse versus time in panel A, and panel B shows a change from an initial entangled state to a final entangled state in response to subjecting a quantum sensor to an echo pulse.
Figure 9:
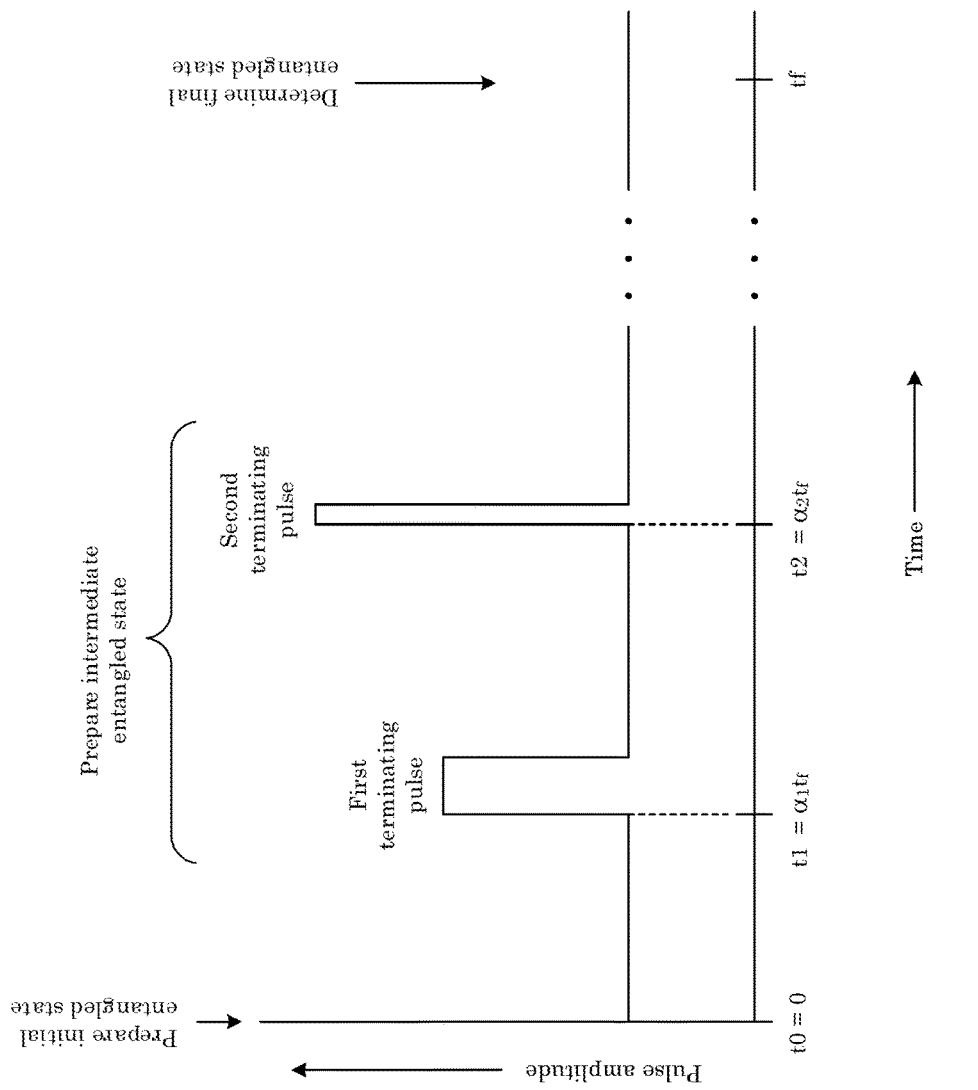
FIG. 9 shows a graph of amplitudes of terminating pulses versus time for subjecting a quantum sensor to a plurality of terminating pulses.
Figure 11:
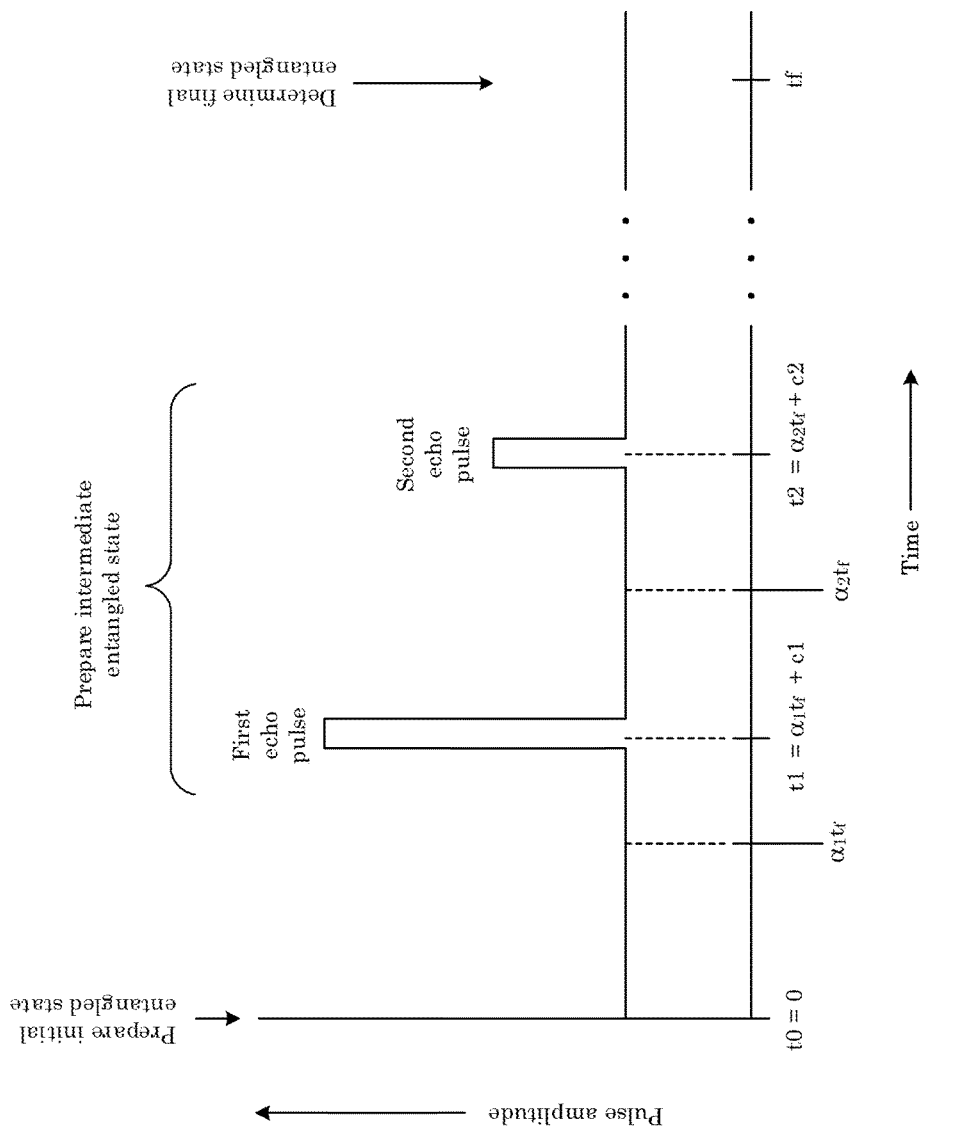
FIG. 11 shows a graph of amplitudes of perturbation pulses versus time for subjecting a quantum sensor to a plurality of echo pulses.
Figure 13:
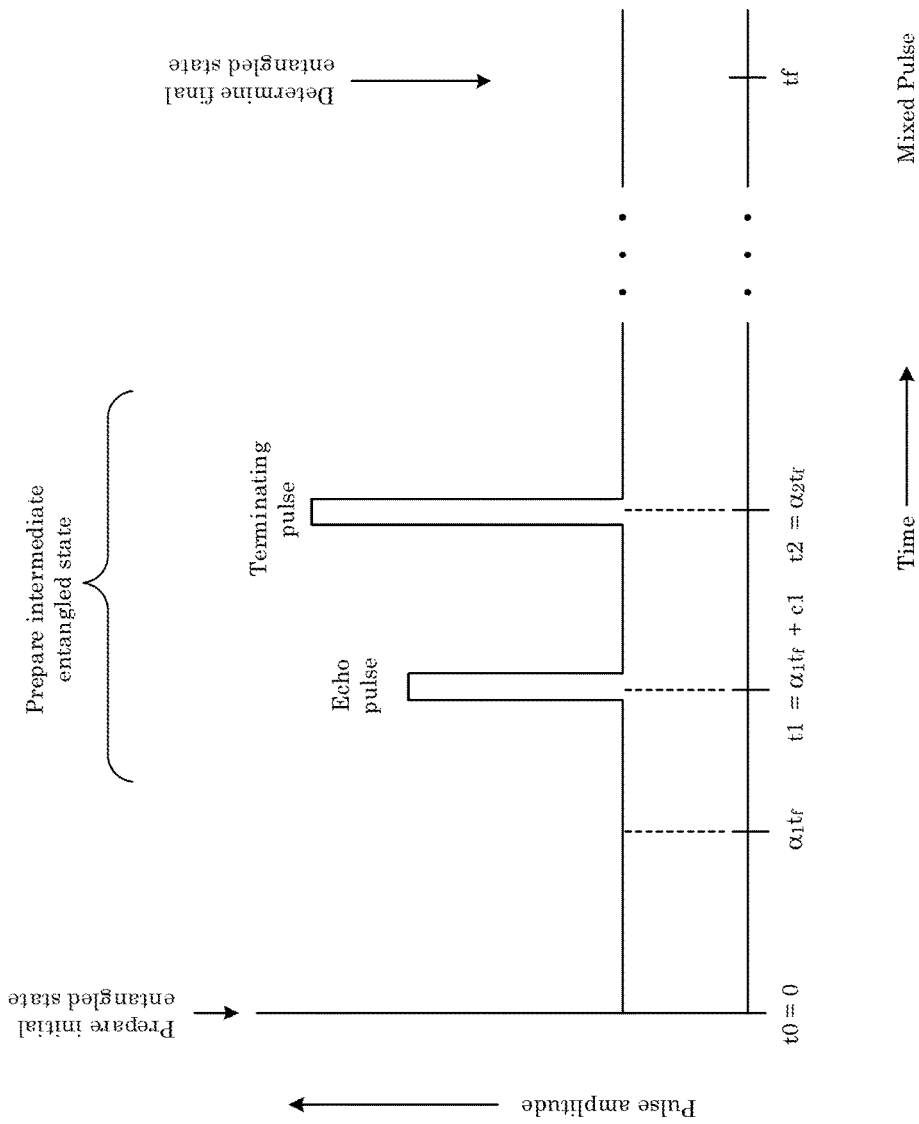
FIG. 13 shows a graph of amplitudes of perturbation pulses versus time for subjecting a quantum sensor to a plurality of perturbation pulses.

With reference to FIG. 5 and FIG. 7, the first perturbation pulse can be a termination pulse as shown in FIG. 5 or an echo pulse as shown in FIG. 7. Further, the process can include subjecting second qudit sensor 10B of quantum sensor 10 to a second perturbation pulse; receiving the second perturbation pulse by second qudit sensor 10B to prepare the second intermediate entangled state of quantum sensor 2, the second intermediate entangled state including a second intermediate linear superposition; changing the first intermediate linear superposition to the second intermediate linear superposition in response to receiving the second perturbation pulse by quantum sensor 2; and determining the final entangled state of the quantum sensor after applying the second perturbation pulse to determine modal amplitude q of inhomogeneous field 50 of analyte 4. In this regard, FIG. 9, FIG. 11, and FIG. 13 show the second perturbation pulse occurring after the first perturbation pulse.

In an embodiment, subjecting first qudit sensor 10A to the first perturbation pulse occurs at a time based on a smallest mode component (i.e., the least $\alpha i$) of modal amplitude q. It is contemplated that mode components $\alpha_i$ can be scaled to the greatest mode components $\alpha_i$ and reordered according to magnitude so that the minimum mode component is $\alpha_1$, and the maximum mode component is $\alpha_N$. In this manner, the first perturbation pulse occurs at first time t1 based on first mode component $\alpha_1$, and second perturbation pulse occurs at second time t2 based on second mode component $\alpha_2$. Swapping the labels of $|0\rangle$ and $|1\rangle$ allows one to deal with negative values of $\alpha i$. If $\alpha i$ are complex, one would repeat the entire procedure twice—once for the real parts, and once for the imaginary parts.

The perturbation pulse can be a terminating pulse or echo pulse. With reference to FIG. 5, which shows a terminating pulse in panel A, an initial entangled state of quantum sensor 2 is prepared at time t0=0, and qudit sensor 10 of quantum sensor 2 is subjected to a terminating pulse at first time t1=$\alpha_i t_f$, which is a time multiple of i-th mode component $\alpha_i$. As a result, as shown in panel B of FIG. 5, the initial entangled state is changed to a final entangled state in response to receipt of the terminating pulse. Here, the initial entangled state can include, e.g., initial linear superposition of first quantum level $|0\rangle$ and second quantum level $|1\rangle$, wherein the initial entangled state is $1/\sqrt{2}[|0\rangle+|1\rangle]$ having energy difference $E=\theta$ between first quantum level $|0\rangle$ and second quantum level $|1\rangle$. The terminating pulse at time t1 transitions second quantum level $|1\rangle$ to third quantum level $|2\rangle$, which is degenerate with first quantum level $|0\rangle$, to produce the final entangled state as $1/\sqrt{2}[|0\rangle+|2\rangle]$ having energy difference $E=0$. For convenience, the state of the qudit sensor is written as a pure state, but it is actually part of an entangled state with other qudit sensors. Moreover, it also contains a phase due to coupling to inhomogeneous field 50. After time t1, the final entangled state of quantum sensor 2 is determined and used to determine modal amplitude q of inhomogeneous field 50 produced by analyte 4.

Figure 6:
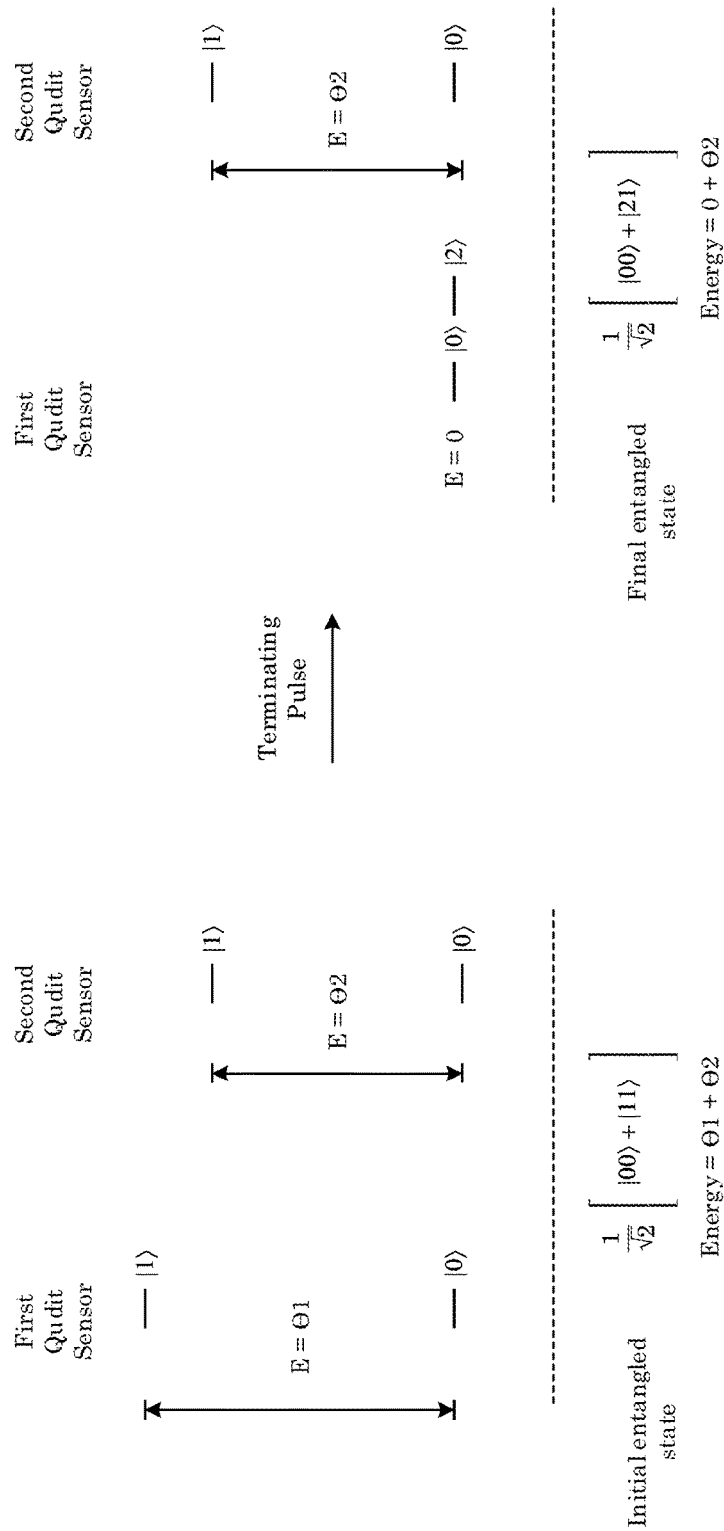
FIG. 6 shows a change from an initial entangled state to a final entangled state in response to subjecting a quantum sensor to a terminating pulse.

In an embodiment, with reference to FIG. 6, quantum sensor 2 includes a first qudit sensor 10A (having quantum levels $|0\rangle$ and $|1\rangle$ with energy difference $E=\theta 1$) and second qudit sensor 10B (having quantum levels $|0\rangle$ and $|1\rangle$ with energy difference $E=\theta 2$), wherein quantum sensor 2 has initial entangled state $1/\sqrt{2}[|00\rangle+|11\rangle]$ having energy difference $E=\theta 1+\theta 2$ between first quantum level $|00\rangle$ and second quantum level $|11\rangle$. A first terminating pulse is subjected to first qudit sensor 10A at time t1=$\alpha_1 t_f$ to produce final entangled state $1/\sqrt{2}[|00\rangle+e^{-it_1(\theta 1+\theta 2)}|21\rangle]$ having energy difference $E=\theta 2$, where the phase was acquired during the time t1 via coupling to inhomogeneous field 50. This entangled state then evolves for time tf-t1 to produce state $1/\sqrt{2}[|00\rangle+e^{-it_f q}|21\rangle]$. It is convenient to undo the terminating pulse at the end to give state $1/\sqrt{2}[|00\rangle+e^{-it_f q}|11\rangle]$, which is then measured.

In an embodiment, perturbation pulse includes an echo pulse. With reference for FIG. 7, which shows an echo pulse in panel A, an initial entangled state of quantum sensor 2 is prepared at time t0, and qudit sensor 10 of quantum sensor 2 is subjected to an echo pulse at first time t1=$\alpha_i t_f$+c, which is after a time multiple of i-th mode component $\alpha_i$ by a selected time amount c=tf$(1-\alpha_i)/2$. As a result, as shown in panel B of FIG. 7, the initial entangled state is changed to a final entangled state in response to receipt of the echo pulse. Here, the initial entangled state can include, e.g., initial linear superposition of first quantum level $|0\rangle$ and second quantum level $|1\rangle$, wherein the initial entangled state is $1/\sqrt{2}[|0\rangle+|1\rangle]$ having energy difference $E=\theta$ between first quantum level $|0\rangle$ and second quantum level $|1\rangle$. The echo pulse at time t1 exchanges second quantum level $|1\rangle$ with first quantum level $|0\rangle$ to produce the final entangled state as $1/\sqrt{2}[|1\rangle+|0\rangle]$ having energy difference $E=-\theta$. For convenience, the state of the qudit sensor is written as a pure state, it is actually part of an entangled state with other qudit sensors and it also contains a phase picked up due to coupling to inhomogeneous field 50. After time t1, the final entangled state of quantum sensor 2 is determined and used to determine modal amplitude q. of quantum sensor 2.

Figure 8:
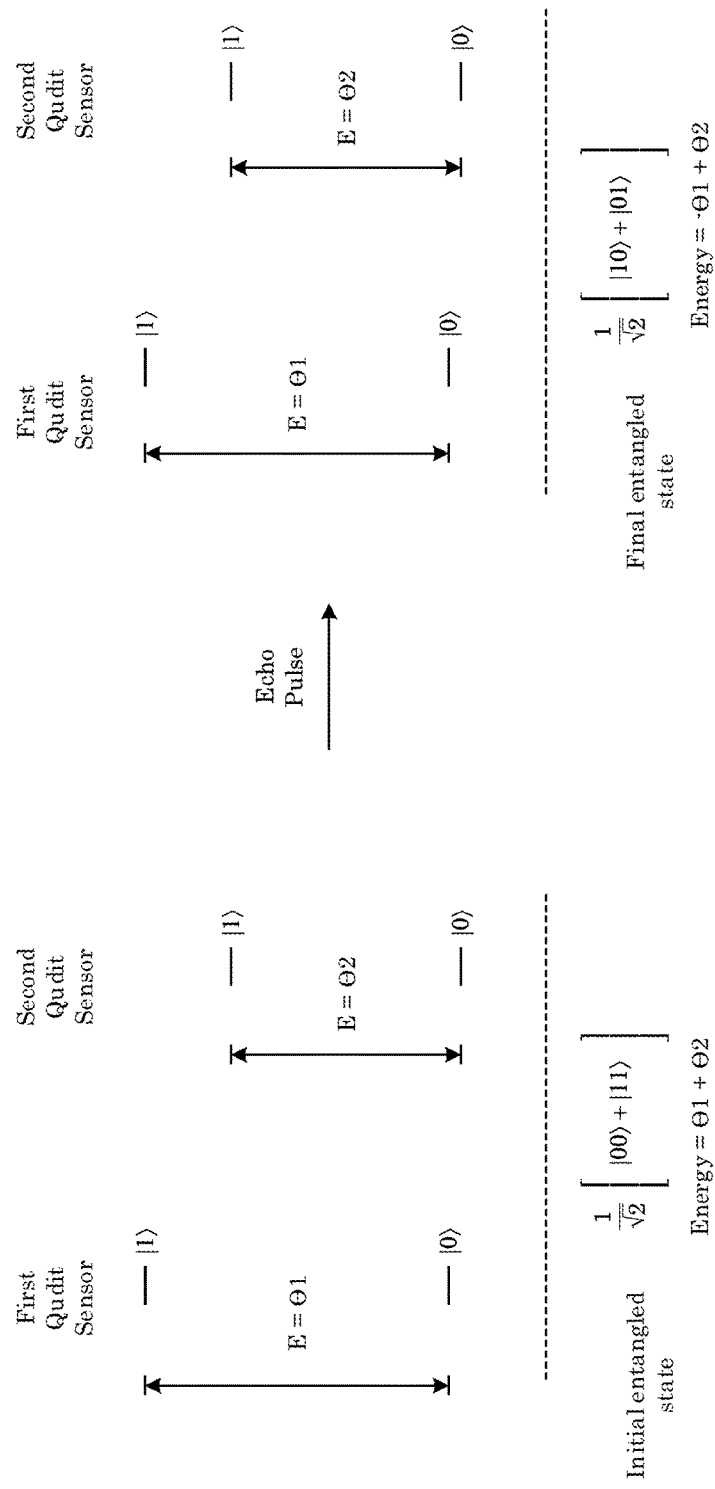
FIG. 8 shows a change from an initial entangled state to a final entangled state in response to subjecting a quantum sensor to an echo pulse.

In an embodiment, with reference to FIG. 8, quantum sensor 2 includes a first qudit sensor 10A (having quantum levels $|0\rangle$ and $|1\rangle$ with energy difference $E=\theta 1$) and second qudit sensor 10B (having quantum levels $|0\rangle$ and $|1\rangle$ with energy difference $E=\theta 2$), wherein quantum sensor 2 has initial entangled state $1/\sqrt{2}[|00\rangle+|11\rangle]$ having energy difference $E=-\theta 1+\theta 2$ between first quantum level $|00\rangle$ and second quantum level $|11\rangle$. A first echo pulse is subjected to first qudit sensor 10A at time t1=$\alpha_1 t_f$+c in which levels of first qudit sensor 10A are exchanged (i.e., $|0\rangle \leftrightarrow |1\rangle$) to produce final entangled state $1/\sqrt{2}[|10\rangle+e^{-it_1(\theta 1+\theta 2)}|01\rangle]$ having energy difference $E=-\theta 1+\theta 2$, where the phase was acquired during the time t1 via coupling to the inhomogeneous field. This entangled state then evolves for time tf-t1 to produce state $1/\sqrt{2}[|00\rangle+e^{-it_f q}|01\rangle]$. It is convenient to undo the echo pulse at the end to give state $1/\sqrt{2}[|00\rangle+e^{-it_f q}|11\rangle]$, which is then measured.

In an embodiment, with reference to FIG. 9, quantum sensor 2 including a plurality of qudits 10 (e.g., 10A, 10B, and the like) is subjected to preparation of an initial entangled state at time t0=0, which is subjected to a plurality of perturbation pulses, e.g., terminating pulses. At time t1, first qudit 10A is subjected to a first terminating pulse to prepare first intermediate entangled state. At time t2, second qudit 10B is subjected to a second terminating pulse to prepare a final entangled state that is subjected to determination for obtaining modal amplitude q. Here, as shown in FIG. 10, the initial entangled state of quantum sensor 2 can be $1/\sqrt{2}[|000\rangle+|111\rangle]$ such that first terminating pulse at time t1 produces intermediate entangled state $1/\sqrt{2}[|000\rangle+e^{-it_1(\theta 1+\theta 2+\theta 3)}|211\rangle]$, which is subjected to second terminating pulse at time t2 to produce final entangled state $1/\sqrt{2}[|000\rangle+e^{-it_1(\theta 1+\theta 2+\theta 3)-i(t_2-t_1)(\theta 2+\theta 3)}|221\rangle]$. This entangled state then evolves for time tf-t2 to produce state $1/\sqrt{2}[|000\rangle+e^{-it_f q}|221\rangle]$. It is convenient to undo the terminating pulses at the end to give state $1/\sqrt{2}[|000\rangle+e^{-it_f q}|111\rangle]$, which is then measured.

Figure 12:
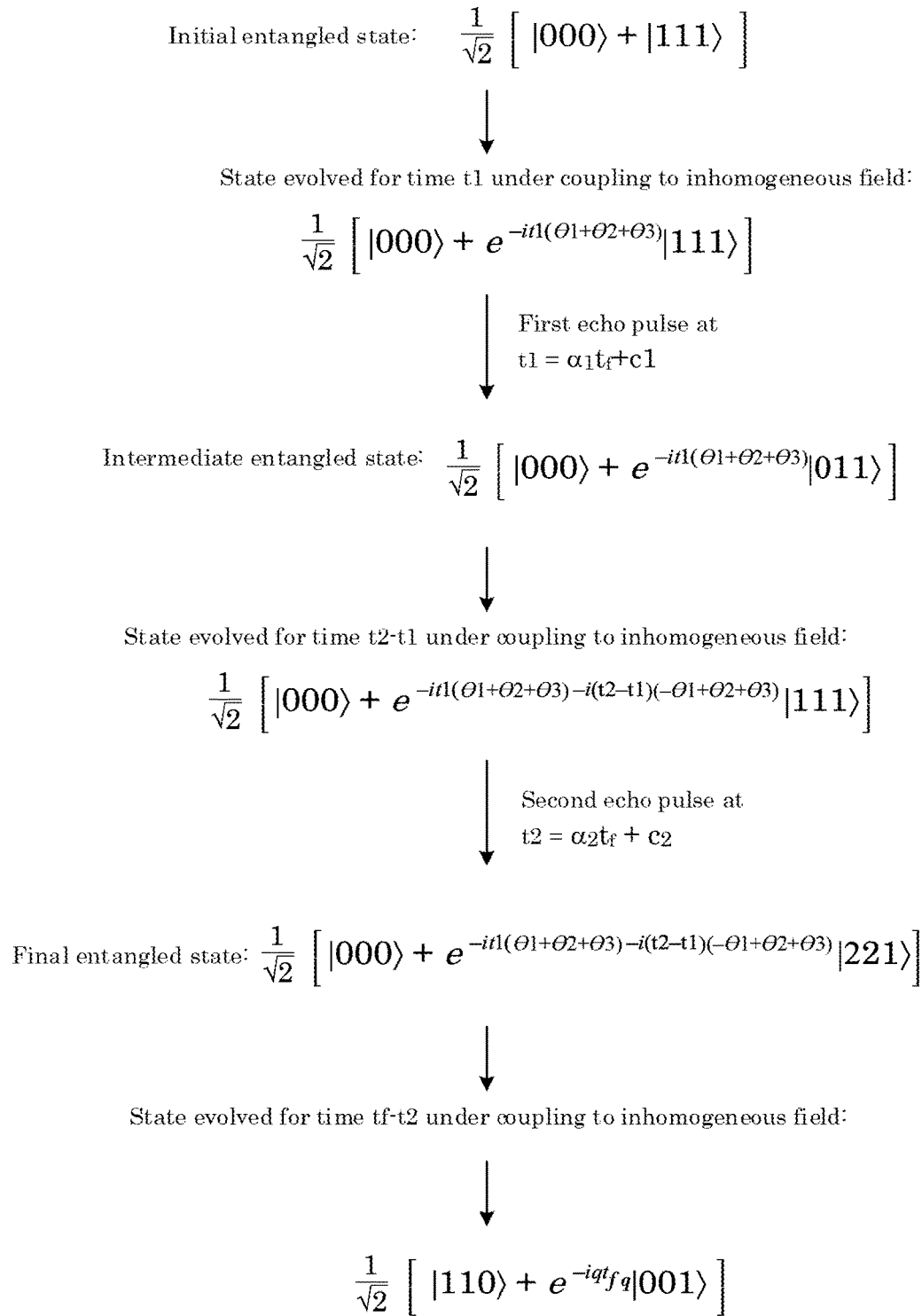
FIG. 12 shows a change from an initial entangled state to a final entangled state through an intermediate entangled state in response to subjecting a quantum sensor to a plurality of echo pulses.

In an embodiment, with reference to FIG. 11, quantum sensor 2 including a plurality of qudits 10 (e.g., 10A, 10B, and the like) is subjected to preparation of an initial entangled state at time t0, which is subjected to a plurality of perturbation pulses e.g., echo pulses. At time t1, first qudit 10A is subjected to a first echo pulse to prepare first intermediate entangled state. At time t2, second qudit 10B is subjected to a second echo pulse to prepare a final entangled state that is subjected to determination for obtaining modal amplitude q. Here, as shown in FIG. 12, the initial entangled state of quantum sensor 2 can be $1/\sqrt{2}[|000\rangle+|111\rangle]$ such that first echo pulse at time t1 produces intermediate entangled state $1/\sqrt{2}[|100\rangle+e^{-it_1(\theta 1+\theta 2+\theta 3)}|011\rangle]$, which is subjected to second echo pulse at time t2 to produce final entangled state $1/\sqrt{2}[|110\rangle+e^{-it_1(\theta 1+\theta 2+\theta 3)-i(t_2-t_1)(-\theta 1+\theta 2+\theta 3)}$ ∥001⟩]. This entangled state then evolves for time tf-t2 to produce state $1/\sqrt{2}[|110\rangle + e^{-it_f q}|001\rangle]$. It is convenient to undo the echo pulses at the end to give state $1/\sqrt{2}[|000\rangle + e^{-it_f q}|111\rangle]$, which is then measured.

Figure 14:
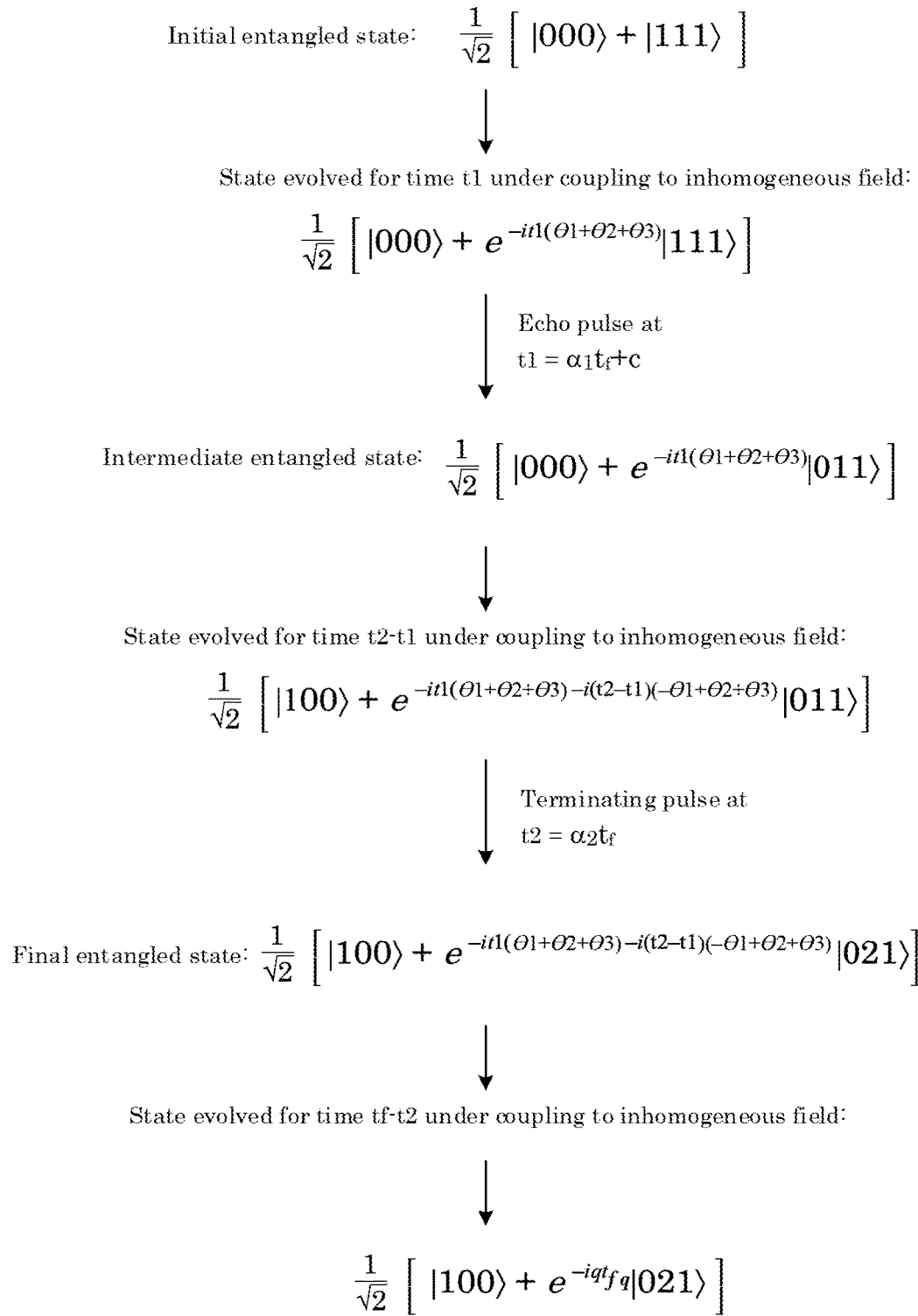
FIG. 14 shows a change from an initial entangled state to a final entangled state through an intermediate entangled state in response to subjecting a quantum sensor to a plurality of perturbation pulses.

In an embodiment, with reference to FIG. 13, quantum sensor 2 including a plurality of qudits 10 (e.g., 10A, 10B, and the like) is subjected to preparation of an initial entangled state at time to, which is subjected to a plurality of perturbation pulses e.g., a combination of echo pulses and terminating pulses. At time t1, first qudit 10A is subjected to an echo pulse to prepare first intermediate entangled state. At time t2, second qudit 10B is subjected to a terminating pulse to prepare a final entangled state that is subjected to determination for obtaining modal amplitude q. is contemplated that, as shown in FIG. 14, the initial entangled state of quantum sensor 2 can be $1/\sqrt{2}[|000\rangle + |111\rangle]$ such that the echo pulse at time t1 produces intermediate entangled state $1/\sqrt{2}[|100\rangle + e^{-it_1(\theta_1+\theta_2+\theta_3)}|011\rangle]$, which is subjected to terminating pulse at time t2 to produce final entangled state $1/\sqrt{2}[|100\rangle + e^{-it_1(\theta_1+\theta_2+\theta_3)-i(t_2-t_1)(-\theta_1+\theta_2+\theta_3)}|021\rangle]$. This entangled state then evolves for time tf-t2 to produce state $1/\sqrt{2}[|100\rangle + e^{-it_f q}|021\rangle]$. It is convenient to undo the perturbation pulses at the end to give state $1/\sqrt{2}[|000\rangle + e^{-it_f q}|111\rangle]$, which is then measured.

Figure 15:
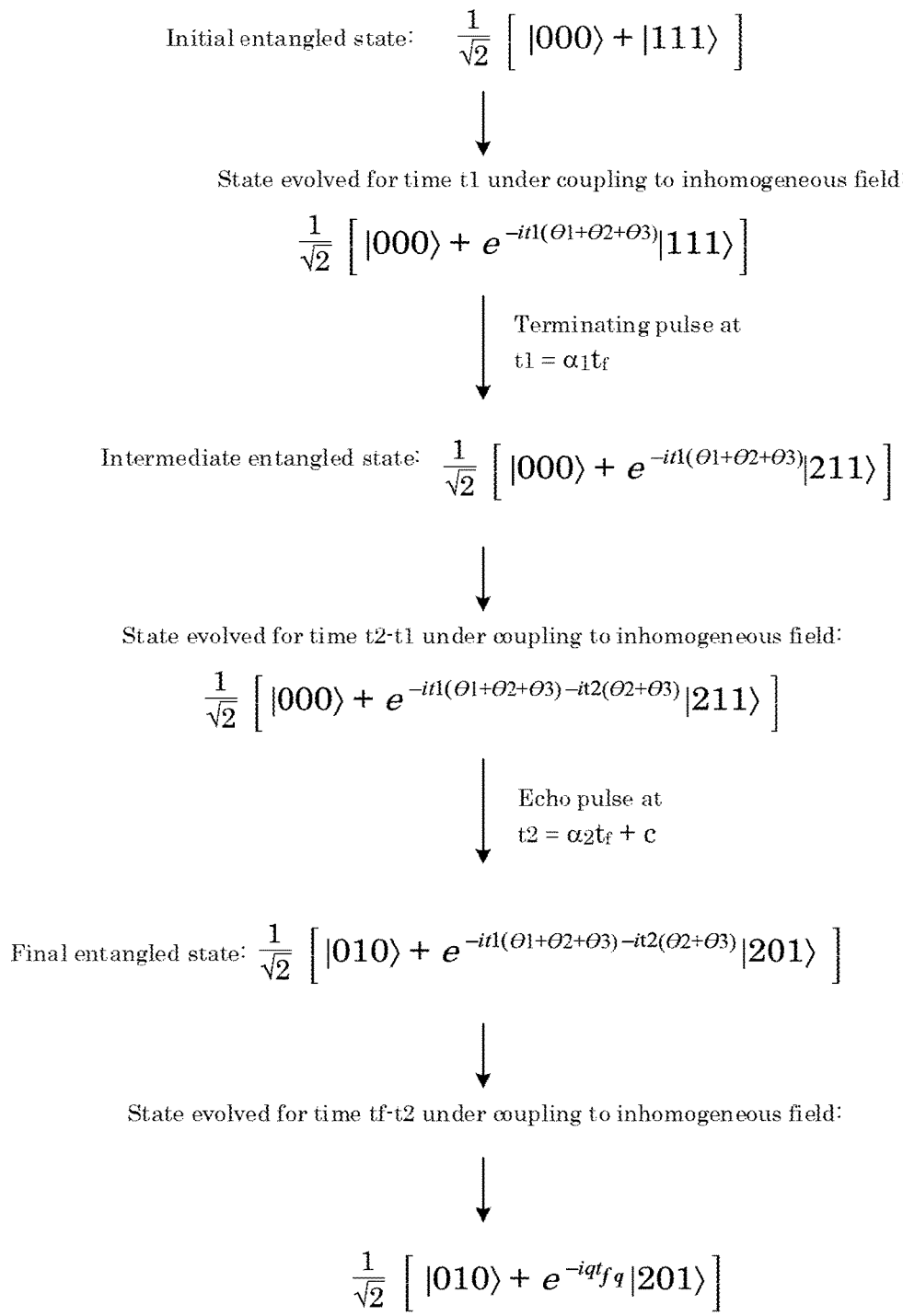
FIG. 15 shows a change from an initial entangled state to a final entangled state through an intermediate entangled state in response to subjecting a quantum sensor to a plurality of perturbation pulses.

In a plurality of perturbation pulses, a sequence of the perturbation pulses can be a selected sequence of terminating pulses in the echo pulses in a selected number of the terminating pulses and echo pulses. In an embodiment, with reference to FIG. 15, initial entangled state of quantum sensor 2 can be $1/\sqrt{2}[|000\rangle + |111\rangle]$ such that the terminating pulse at time t1 produces intermediate entangled state $1/\sqrt{2}[|000\rangle + e^{-it_1(\theta_1+\theta_2+\theta_3)}|211\rangle]$, which is subjected to an echo pulse at time t2 to produce final entangled state $1/\sqrt{2}[|010\rangle + e^{-it_1(\theta_1+\theta_2+\theta_3)-i(t_2-t_1)(\theta_2+\theta_3)}|201\rangle]$. This entangled state then evolves for time tf-t2 to produce state $1/\sqrt{2}[|010\rangle + e^{-it_f q}|201\rangle]$. It is convenient to undo the perturbation pulses at the end to give state $1/\sqrt{2}[|000\rangle + e^{-it_f q}|111\rangle]$, which is then measured.

Quantum sensor 2, system 100, and processes herein have numerous advantageous and beneficial properties. In an aspect, the article and process provide the best measurement of the modal amplitude allowed by quantum mechanics, i.e., either the fastest for desired precision or the most precise for a given measurement time. They also provide a secure way of measuring the modal amplitude: as long as an eavesdropper has no access to the measurement results of at least one qudit sensor, her or she will have no information about the modal amplitude. The article and the process also allow one to optimally measure modal amplitudes of combinations of fields such as electric field at one qudit sensor, magnetic field at another qudit sensor, and temperature at a third one.

The articles and processes herein are illustrated further by the following Example, which is non-limiting.

EXAMPLE

Optimal and Secure Measurement Protocols for Quantum Sensor Networks.

Studies of quantum metrology have shown that the use of many-body entangled states can lead to an enhancement in sensitivity when compared to unentangled states. In this Example, we quantify the metrological advantage of entanglement in a setting where the measured quantity is a linear function of parameters individually coupled to each qubit. We first generalize the Heisenberg limit to the measurement of non-local observables in a quantum network, deriving a bound based on the multi-parameter quantum Fisher information. We then describe a measurement protocol that uses Greenberger-Horne-Zeilinger (GHZ) states or spin-squeezed states and show that for GHZ states the protocol is optimal, i.e., it saturates our bound. In this respect, nanoscale magnetic resonance imaging is a use for this technology.

Entanglement is a valuable resource in precision measurement, as measurements using entangled probe systems have fundamentally higher optimal sensitivity than those using unentangled states. A generic measurement using N unentangled probes will have a standard deviation from the true value asymptotically proportional to $1/\sqrt{N}$. By using N maximally entangled probes, a single parameter coupled independently to each probe system can be measured with an uncertainty proportional to $1/N$. This is the best possible scaling consistent with the Heisenberg uncertainty principle, and is known as the Heisenberg limit. The procedure can also be reversed-enhanced sensitivity to disturbances can provide experimental evidence of entanglement.

Measurements making use of entanglement usually couple one parameter to N different systems. However, the emerging potential of long-range quantum information opens avenues for metrology and entanglement distribution. The ability to distribute entanglement across spatially separated regions provides loophole-free tests of Bell's inequality. In this Example, we are interested in coupling N parameters to N different systems, which may be spatially separated, and measuring a linear function of all of them (see FIG. 16, FIG. 17, FIG. 18, and FIG. 19) such as a single mode of a spatially varying field. Such measurements are applicable in geodesy, geophysics, medical imaging, and the like, including nanoscale nuclear magnetic resonance (NMR) imaging.

The modal amplitude function q measured is a weighted sum of deterministic individual parameters $\theta_i$, where i indexes the individual systems and each weight is denoted $$q = \sum_{i=1}^{N} \alpha_i \theta_i = \vec{\alpha} \cdot \vec{\theta}. \tag{1}$$

Figure 17:
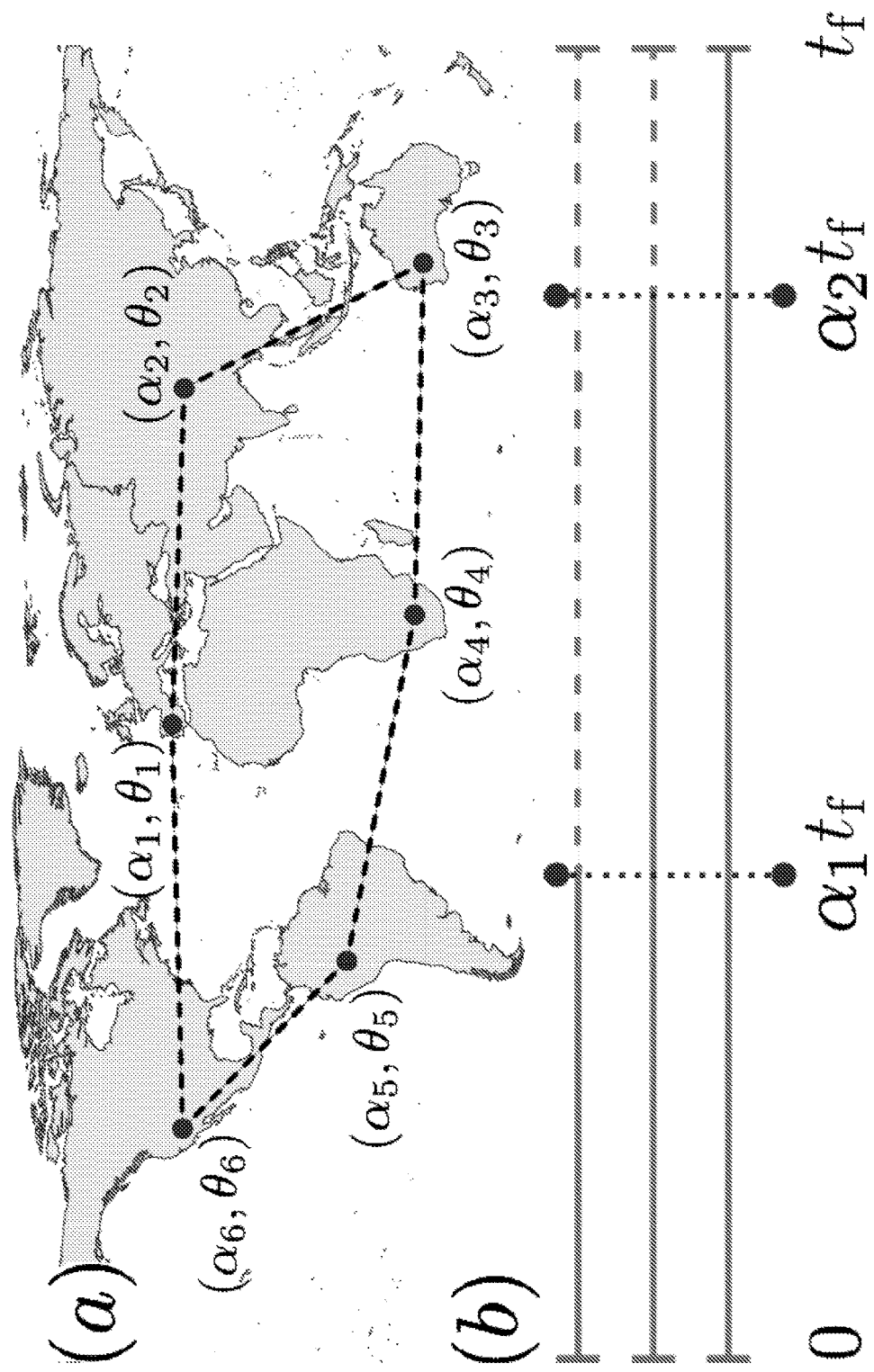
FIG. 17 shows an analyte that includes a plurality of continents disposed proximate to a quantum sensor in panel A, and panel B shows a time over which the quantum sensor is subjected to a plurality of terminating pulses.
Figure 18:
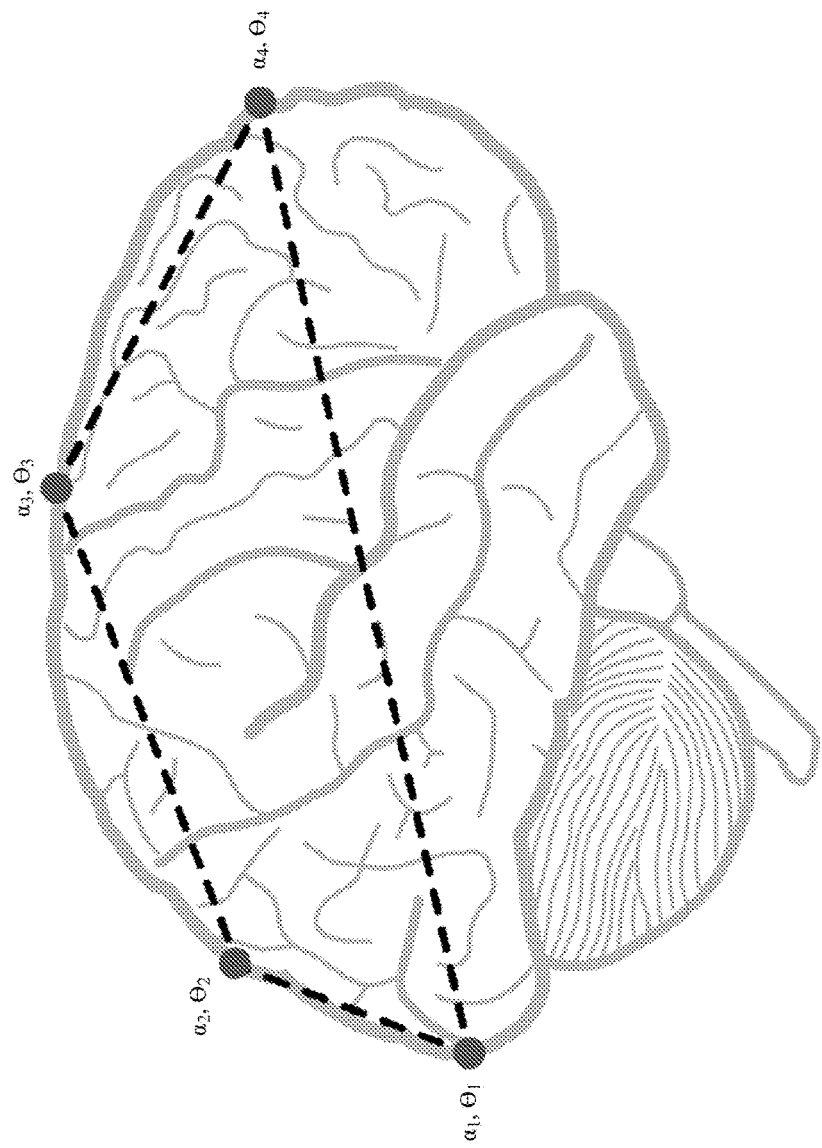
FIG. 18 shows an analyte that includes a brain disposed proximate to a quantum sensor.
Figure 19:
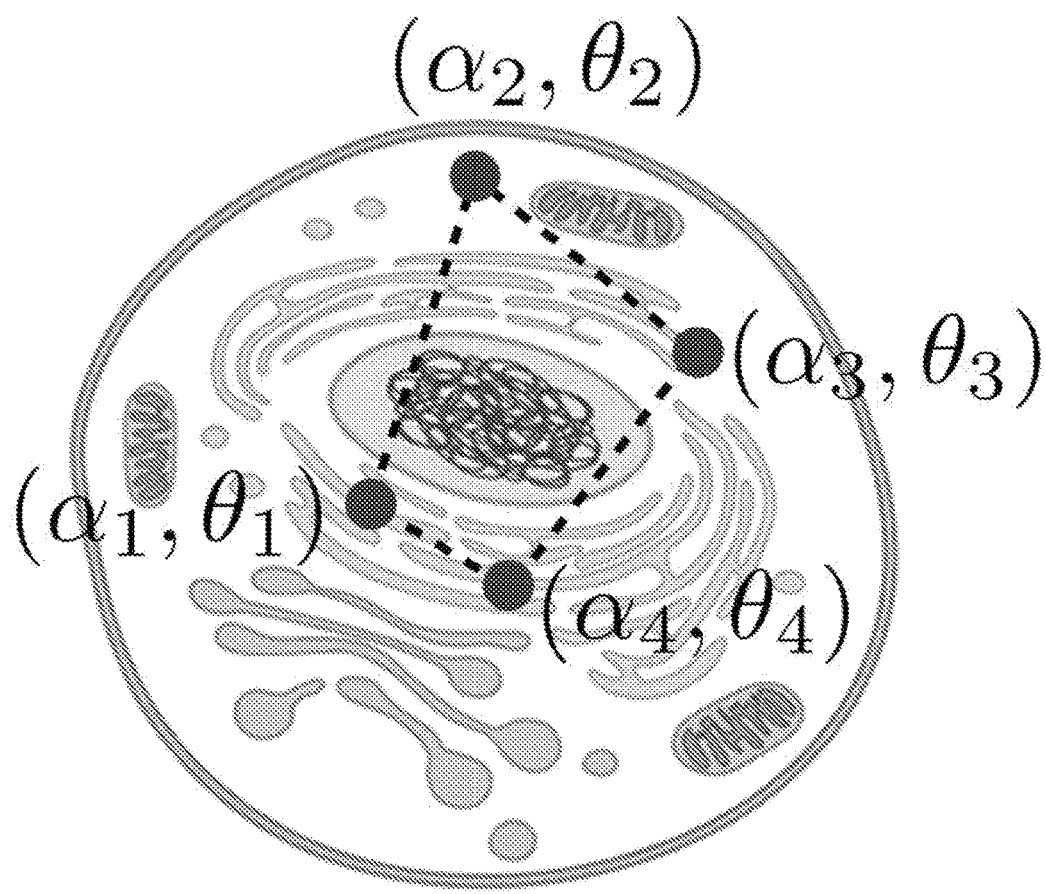
FIG. 19 shows an analyte that includes a cell disposed proximate to a quantum sensor.

Panel A of FIG. 16 and FIG. 17 as well as FIG. 18 and FIG. 19 show a network setup for a molecule (in a nanoscale NMR setting), for the earth, for the brain, and for a cell, respectively. With regard to FIG. 16, qudit sensors (also referred to herein as nodes) are located at different points relative to a large molecule and provide an entangled state for a quantum sensor. At each node, there is an unknown parameter $\theta_i$ and a known relative weight $\alpha_i$. We are concerned with estimating $\vec{\alpha} \cdot \vec{\theta}$. Panels B of FIG. 16 and FIG. 17 show partial time evolution for three qubits of a quantum sensor. Solid line segments of the timeline represent periods when a qubit is evolving due to coupling to the local parameter $\theta_i$, while dashed line segments represent periods after the qubit stops evolving. The switches due to a perturbation pulse (e.g., a terminating pulse) occur at times corresponding to the qubits' weights in the final linear combination. The weight of the last qubit is $\alpha_3=1$.

In this Example, we characterize the advantage entanglement provides in this setting and construct an optimal strategy equivalent to turning some qubits' evolution "on" and "off" for time proportional to the weight with which their parameter contributes to the function q (see panel B of FIG. 16 and FIG. 17). With this scheme of "partial time evolution," a linear function can be measured with the minimum variance permitted by quantum mechanics, which can be viewed as an extension of the Heisenberg limit to linear combinations. This method can protect the secrecy of the result, allowing the network as a whole to perform a measurement without eavesdroppers learning any details of $\vec{\alpha} \cdot \vec{\theta}$.

We consider a system in which there are N sensor nodes. Each sensor node i possesses a single qubit coupled to an unknown parameter $\theta_i$ unique to each node. We suppose that the state evolves unitarily under the Hamiltonian $$\hat{H} = \tilde{H}(t) + \sum_{i=1}^{N} \frac{1}{2}\theta_i \hat{\sigma}_i^z. \qquad (2)$$

Here, $\tilde{H}(t)$ is a selected time-dependent control Hamiltonian chosen with regard to information we wish to obtain about an inhomogeneous field of an analyte such as the molecule and that may include coupling to additional ancilla qubits. We wish to measure the quantity q defined in Eq. (1). We assume that $\forall i: |\alpha_i| \leq 1$ and additionally that there is at least one $\alpha_i$ such that $\alpha_i = 1$. These conditions simply set a scale for the function, and for an arbitrary $\vec{\alpha}$ all that is needed is division by the largest $\alpha_i$ to meet this requirement. As an example, a network with two nodes interested in measuring the contrast between those nodes would set $\vec{\alpha} = (1,-1)$ to measure $\theta_1 - \theta_2$. We would like to establish how well an arbitrary measurement of $\vec{\alpha} \cdot \vec{\theta}$ can be made and what the best measurement protocol is for doing so. As used herein, "protocol" refers to an input state we begin with, what auxiliary control Hamiltonian $\tilde{H}(t)$ is implemented, and how a final measurement is made.

We define the quality of measurement in terms of an estimator, Q, constructed, e.g., from experimental data. Operators are denoted with hats, quantities by lowercase, and corresponding estimators by uppercase. We assume that the estimator is unbiased, so that its expectation value is the true value E[Q]=q. A metric for the quality of the measurement is the average squared error, or variance, of the estimator, $$\mathrm{Var}Q = E[(Q-q)^2]. \qquad (3)$$

If measurements of $\theta_i$ can be made locally with accuracy $\mathrm{Var}\Theta_i$ for an estimator $\Theta_i$, then we could compute the linear combination by local measurements and classical computation. In this case, the variance is given by classical statistical theory as $\mathrm{Var}Q = \|\vec{\alpha}\|^2 \mathrm{Var}\Theta_0$ assuming that $\mathrm{Var}\Theta_i$ is identical at each site and equal to $\mathrm{Var}\Theta_0$. A measurement of an individual $\theta_i$ in Eq. (2) can be made in time t with a variance of $1/t^2$. Therefore, our entanglement-free figure of merit is $$\mathrm{Var}Q \geq \frac{\|\vec{\alpha}\|^2}{t^2}. \qquad (4)$$

We consider this the standard quantum limit for networks. To compare to the typical case where N independent qubits measure a single parameter, consider the average $\bar{\theta}$, which is equivalent to setting all $\alpha_i = 1$ and then using $\bar{\Theta} = Q/N$ to obtain $\mathrm{Var}\bar{\Theta} = 1/Nt^2$.

Parameter estimation is performed on a quantum system evolving under some set of parameters $\{\theta_i\}$ linearly coupled to sensor qubits as in Eq. (2). Although we are interested in measuring a single number, we treat a system that has many parameters in the evolution and therefore use a multi-parameter theory. From classical estimation theory, given a probability distribution p(z) over a set of outcomes z that depends on a number of parameters, estimators of the parameters obey the Cramer-Rao inequality, $$\Sigma \geq \frac{F^{-1}}{M}. \qquad (5)$$

Here, M is the number of experiments performed, F is the Fisher information matrix (see below), and $\Sigma$ is the covariance matrix, where $\Sigma_{ij} = E[(\Theta_i - \theta_i)(\Theta_j - \theta_j)]$. The inequality is a matrix inequality, meaning that $M\Sigma - F^{-1}$ is positive semidefinite. We will concern ourselves with the single-shot Fisher information, and set M=1 from now on. The Fisher information matrix captures how each parameter changes the probability distribution of outcomes, $$F_{ij} = \int p(z) \left(\frac{\partial \ln p(z)}{\partial \theta_i}\right)\left(\frac{\partial \ln p(x)}{\partial \theta_j}\right) dz. \qquad (6)$$

This bound is a purely classical statement about probability distributions, and is saturated asymptotically using a maximum-likelihood estimator. Quantum theory bounds the probability distributions that can result from a state evolved under a parameter-dependent unitary operation.

Our parameters in the Fisher information matrix F are the individual $\theta_i$, while the quantity we want to estimate is some combination of these, $\vec{\alpha} \cdot \vec{\theta}$. To formulate the appropriate Cramer-Rao bound in this case, we write a new Fisher information matrix, G, where the parameters are recast in a new basis which includes $\vec{\alpha}$, $$G_{ij} = \int p(z) \left(\frac{\partial \ln p(z)}{\partial (\vec{\alpha}^{(i)} \cdot \vec{\theta})}\right)\left(\frac{\partial \ln p(z)}{\partial (\vec{\alpha}^{(j)} \cdot \vec{\theta})}\right) dz. \qquad (7)$$

Here, $\vec{\alpha}^{(i)}$ represents an element of a new set of N real vectors which span the entire N-dimensional space. We designate the first element of that set, $\vec{\alpha}^{(1)}$, as the $\vec{\alpha}$ we are interested in. The Cramer-Rao bound on our quantity of interest is $$\mathrm{Var}Q \geq (G^{-1})_{11}. \qquad (8)$$

Using the chain rule it can be shown that if we arrange the vectors $\vec{\alpha}^{(i)}$ into a matrix A such that $A_{ij} = \vec{\alpha}_j^{(i)}$, then F is related to G by the transformation $F = A^T GA$. It then follows that $(G^{-1})_{11} = \vec{\alpha}^{(1)T} F^{-1} \vec{\alpha}^{(1)} = \vec{\alpha}^T F^{-1} \vec{\alpha}$, so that $$\mathrm{Var}Q \geq \vec{\alpha}^T F^{-1} \vec{\alpha}. \qquad (9)$$

Note that although we began by considering the full covariance matrix, we now focus on just a single scalar $\vec{\alpha}^T F^{-1} \vec{\alpha}$ because our quantity of interest is a single linear transformation of the original parameters. Since F is positive semidefinite, F is Hermitian. We can then write the following for an arbitrary real $\vec{b}$ by invoking the Cauchy-Schwarz inequality:

$$\|\sqrt{F^{-1}}\vec{\alpha}\|^2 \|\sqrt{F}\vec{b}\|^2 \geq \|\vec{\alpha}^T \sqrt{F^{-1}}\sqrt{F}\vec{b}\|^2. \qquad (10)$$

Taking $\vec{b}$ to be the bth element of the standard basis gives $$\operatorname{Var} Q \geq \vec{\alpha}^T F^{-1} \vec{\alpha} \geq \frac{\alpha_b^2}{F_{bb}}. \qquad (11)$$

$F_{bb}$ is the Fisher information for a single parameter. For a time-dependent control Hamiltonian $\tilde{H}(t)$, including those with ancilla qubits, $F_{bb} \leq t^2 \|\hat{h}_b\|_s^2$. Here $\|\hat{h}_b\|_s$ is the operator seminorm (difference between the largest and smallest eigenvalues) of the generator corresponding to parameter $\theta_b$. Our final bound comes from applying this condition and recognizing that the formula must hold for all b:

$$\operatorname{Var} Q \geq \max_b \frac{\alpha_b^2}{t^2 \|\hat{h}_b\|_s^2}. \qquad (12)$$

Eq. (12) remains true no matter what time-dependent control $\tilde{H}(t)$ is applied. In Eq. (2), $h_b = \frac{1}{2}\hat{\sigma}_b^z$, $\|\tilde{h}_b\|_s = 1$, and we find a bound, $$\operatorname{Var} Q \geq \frac{1}{t^2}. \qquad (13)$$

Here we have also used the fact that the largest $\alpha_i = 1$. If we want to calculate an average of the $\theta_i$, then all qubits are equally weighted and the desired quantity is $\bar{\theta} = q/N$, so $\operatorname{Var} \bar{\Theta} \geq 1/N^2 t^2$ and we reproduce the desired Heisenberg scaling. However, note that if we wanted to calculate only a single $\theta_i$, then we would not scale coefficients at all. Our bound allows us to explore the full range of possible $\vec{\alpha}$ between these two extremes. Compared to the bound on unentangled states [Eq. (4)], Eq. (12) simply picks out the largest contribution due to uncertainty from a single site. Equation (12) can be viewed as an extension of the usual Heisenberg bound to the case of combinations of parameters.

Figure 20:
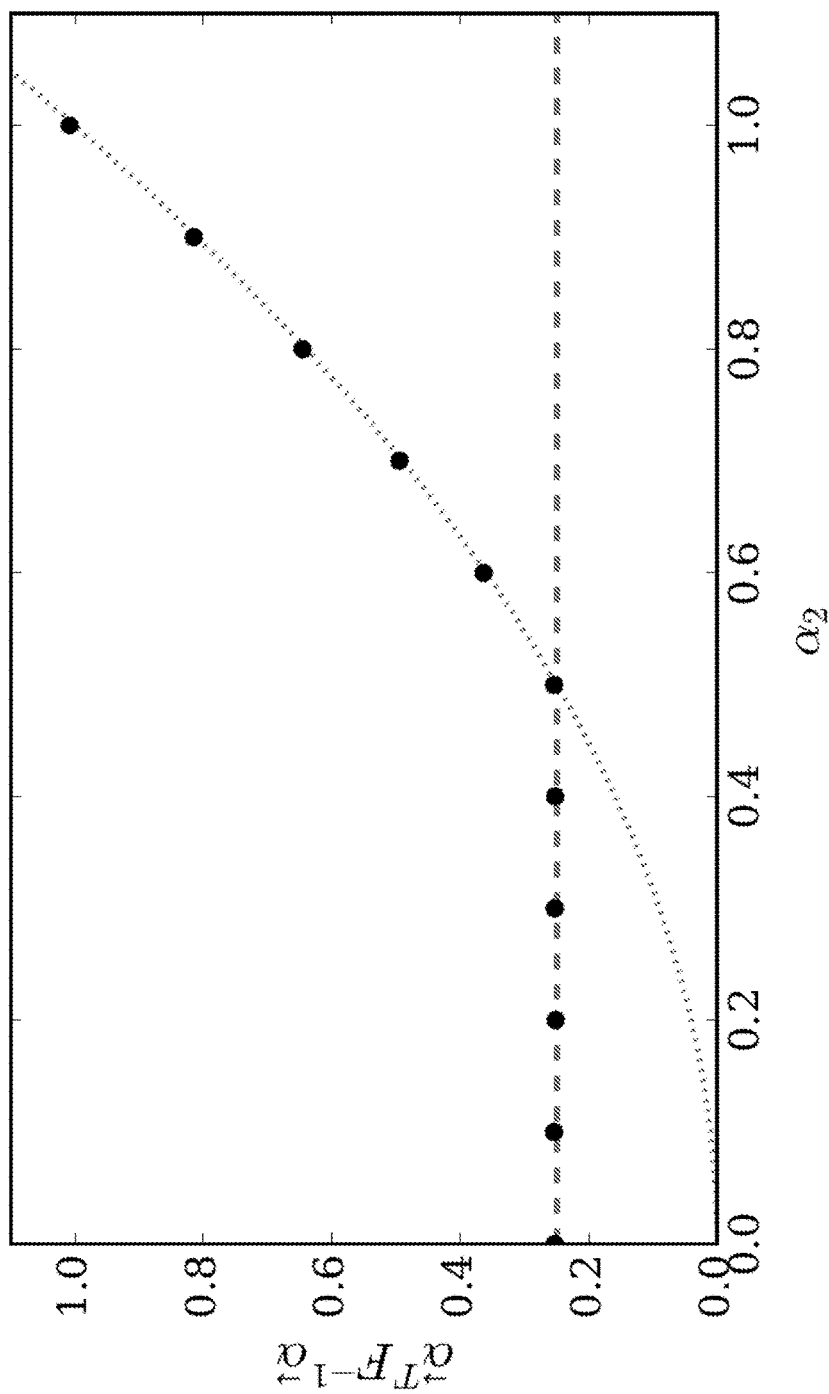
FIG. 20 shows a graph of uncertainty in a measurement of a modal amplitude versus a component of a mode.

We can verify that the above argument is correct by optimizing over the space of all control Hamiltonians $\tilde{H}(t)$. We consider a two-qubit sensor network with no ancillas. The Hamiltonians we $\vec{\alpha}^T F^{-1} \vec{\alpha}$ optimize over include enough operators to provide universal control on two qubits, meaning we can effectively modify the input state as well as the final measurement basis in order to optimize the Fisher information. To test the form of our bound, Eq. (12), which depends both on relative weights of each parameter and the underlying generator, we couple $\theta_1$ to a generator $\hat{\sigma}_1^z$ which has $\|\hat{\sigma}_1^z\|_s = 2$. We leave the second qubit coupled to a generator $\frac{1}{2}\hat{\sigma}_2^z$ as in Eq. (2). The bound corresponding to the first qubit from Eq. (12) is $\alpha_1^2/4t^2$ and that of the second qubit is $\alpha_2^2/t^2$. In our numerics, we set $\alpha_1 = t = 1$, meaning the two bounds are $\frac{1}{4}$ and $\alpha_2^2$. Our analytic result leads us to believe therefore that if $\alpha_2^2 > \frac{1}{4}$, the minimum possible variance should be $\alpha_2^2$. However, if $\alpha_2^2 < \frac{1}{4}$, then the lower bound should be $\frac{1}{4}$. That behavior is precisely what we find through the numerical optimization shown in FIG. 20, confirming Eq. (12). FIG. 20 shows numerical optimization of for two qubits with $\alpha 1 = 1$ compared to the bound predicted by our analytic result. Each point is generated by running a gradient descent algorithm until convergence; the control parameters begin at small random values. The dashed (dotted) line is the analytic bound derived from the first (second) qubit. As $\alpha 2$ increases, the second qubit becomes the source of the relevant bound.

We now present a protocol that saturates the bound of Eq. (13) and is therefore optimal. We start by considering an N-qubit Greenberger-Horne-Zeilinger (GHZ) state:

$$\frac{1}{\sqrt{2}}(|0\rangle^{\otimes N} + |1\rangle^{\otimes N}). \qquad (14)$$

Under $\hat{\sigma}^z$ evolution, each $|1\rangle$ accumulates a phase relative to $|0\rangle$. By allowing qubits to accumulate phase proportional to the desired weight $\alpha_i$, we obtain a final state in which $|1\rangle^{\otimes N}$ has accumulated a total phase of $\vec{\alpha} \cdot \vec{\theta} t$ relative to $|0\rangle^{\otimes N}$. We refer to our protocol as "partial time evolution" because it relies on a qubit undergoing evolution for a fraction of the total measurement time (see, e.g., FIG. 16). We can realize this by applying an echo pulse $\hat{\sigma}_1^x$ to a qubit at time $t_i = t(1 + \alpha_i)/2$ so that the qubit evolution will be identical to evolving it for a time $\alpha_i t$. Note that if there is a fixed experimental time t, this scheme can realize values of $\alpha_i \in [-1, 1]$, which motivates our restrictions on the values of individual $\alpha_i$. Specifying this sequence of gates identifies the $\tilde{H}(t)$ which defines the protocol. The result of this protocol is an effective evolution according to the unitary operator $$U(t) = e^{-i\frac{t}{2}\sum_{i=1}^{N} \alpha_i \theta_i \hat{\sigma}_i^z}. \qquad (15)$$

Under this evolution, the final state is:

$$\frac{1}{\sqrt{2}}\left(e^{-i\frac{t}{2}q}|0\rangle^{\otimes N} + e^{i\frac{t}{2}q}|1\rangle^{\otimes N}\right). \qquad (16)$$

Now we make a measurement of the overall parity of the state, $\hat{P} = \otimes_{i=1}^{N} \hat{\sigma}_i^x$. The measurement be performed locally at each site. Measurement of the time-dependent expectation value $\langle \hat{P} \rangle(t)$ allows for the estimation of Q with accuracy $$\operatorname{Var} Q = \frac{\operatorname{Var} \hat{P}(t)}{(\partial \langle \hat{P} \rangle / \partial q)^2} = \frac{\sin^2 qt}{t^2 \sin^2 qt} = \frac{1}{t^2}, \qquad (17)$$

saturating the bound in Eq. (13) and FIG. 20.

The optimal measurement is one in which most qubits spend some of the measurement time idle. Since more time yields more signal, intuition suggests that the most effective strategy would make better measurements on the less-weighted qubits rather than keep them off for much of the measurement time. For example, by disentangling a qubit from the larger state halfway through the protocol, a separate measurement could be made on $\theta_1 + \frac{1}{2}\theta_2$ and $\frac{1}{2}\theta_2$, which appears to yield more information than just measuring the quantity of interest $\theta_1 + \frac{1}{2}\theta_2$. This reasoning fails because we assume no prior knowledge on the individual parameters. If $\theta_2$ is known to high precision, but we lack any information about $\theta_1$, there is no way to use our certainty about $\theta_2$ to improve an estimate of $\theta_1 + \frac{1}{2}\theta_2$. Because we consider no prior knowledge about the individual parameters, a measurement of the entire function is usable and our scheme is optimal in this case. Our bound applies in the regime of asymptotically many measurements and in that setting our scheme will also saturate it.

One advantage of this protocol is that an eavesdropper cannot learn the result of the network measurement by capturing a subset of the nodes' $\hat{\sigma}^x$ measurement results. This privacy can be shown by tracing out the first qubit in Eq. (16), which leaves no phase information in the resulting mixed state. The central node can receive the measurement outcomes from all other nodes but keep its own secret, and no eavesdropper is able to extract information from the broadcasted results. This is true even if the central node's qubit is unweighted (i.e., $\alpha_j=0$), which follows simply from the properties of the GHZ state. Spin-squeezed states are also viable inputs to the protocol although they lack the security property introduced above.

Many applications of entangled sensor networks may emerge as distributed entanglement becomes easier to achieve. In this Example, we describe an application of the protocol to nanoscale nuclear magnetic resonance (NMR) as a form of molecular microscopy. NMR provides chemical composition of molecular structures and enables medical imaging. The spatial resolution of NMR was limited by a few micrometers until the advent of nitrogen-vacancy (NV) center magnetometers. These magnetometers are sensitive to nanotesla magnetic fields with spatial resolution on the nanometer scale and can be used to image molecules or single proteins deposited on a diamond layer with embedded NV centers.

Here, a nanoscale NMR application provides a setting for entanglement-enhanced sensor networks. The electronic spin associated with an NV center in diamond can be operated as a two-level system whose free evolution results in the accumulation of phase dependent on the local magnetic field. NV centers are useful platforms for quantum information processing. Our protocol is useful for studies of chemical or magnetic dynamics because the measurement timescale may be much shorter than the decoherence time of the GHZ state, making our noise-free treatment applicable.

Linear combinations of spatially separated field values are interesting measurement quantities in nanoscale NMR. Measurements could be performed more accurately using entangled NV sensors. In addition, our entanglement scheme can perform simple subtraction of the signal between two qubits. This allows common mode noise subtraction between a sensor qubit and another qubit exposed only to environmental noise. In general, even if a full GHZ state of all sensors is not feasible, smaller clusters of entangled sensors can still enhance sensitivity.

Entanglement-enhanced imaging of objects larger than single molecules can be made with the protocol. Detecting the firing of a single animal neuron with accuracy near the standard quantum limit is contemplated.

In this Example, we presented a measurement protocol for quantum networks which is useful for measuring linear combinations of parameters and developed a Heisenberg limit for the optimal estimation of linear combinations. Our protocol can be considered a generalization of entanglement-enhanced Ramsey spectroscopy for the measurement of spatially varying quantities. Although magnetometry and nanoscale NMR are discussed in this Example, the protocol is useful for measuring spatially varying quantities in contexts such as gravimetry, spectroscopy, rotation sensing, and the like. Further, the protocol can be applied in any setting where Ramsey spectroscopy can be applied if the quantity of interest is nonlocal. Many of these schemes for quantum sensing rely on coherence in photonic, rather than atomic, degrees of freedom, such as spectroscopic microscopy. The protocol herein provides a framework for treatment of sensor networks which is applicable to photonic systems and others.

Embodiments of the subject matter and the operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions, encoded on a computer storage medium for execution by, or to control the operation of, data processing apparatus. Alternatively, or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more computers executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Computers suitable for the execution of a computer program include, by way of example, can be based on general or special purpose microprocessors or both, workstations, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic; magneto-optical disks, optical disks, USB drives, and so on. However, a computer need not have such devices. Moreover, a computer can be embedded in another device, e.g., a mobile telephone, a personal digital assistant (PDA), a microwave oven, mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The central processing unit and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks). Such interconnects may involve electrical cabling, fiber optics, or be wireless connections.

The computing system can include clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specific implementation details, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the invention have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

Reference throughout this specification to "one embodiment," "particular embodiment," "certain embodiment," "an embodiment," or the like means that a particular feature, structure, or characteristic described in connection with the embodiment is included in at least one embodiment. Thus, appearances of these phrases (e.g., "in one embodiment" or "in an embodiment") throughout this specification are not necessarily all referring to the same embodiment, but may. Furthermore, particular features, structures, or characteristics may be combined in any suitable manner, as would be apparent to one of ordinary skill in the art from this disclosure, in one or more embodiments.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." Further, the conjunction "or" is used to link objects of a list or alternatives and is not disjunctive; rather the elements can be used separately or can be combined together under appropriate circumstances. It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

What is claimed is:

1. A process for determining a modal amplitude of an inhomogeneous field of an analyte, the process comprising:
preparing an initial entangled state of a quantum sensor, the initial entangled state comprising:
a first quantum level; and
a second quantum level,
the initial entangled state being an initial linear superposition of the first quantum level and the second quantum level, and
the quantum sensor comprising a plurality of qudit sensors in which each qudit sensor comprises an energy difference between a plurality of quantum levels of the qudit sensor, the energy difference being linearly dependent on a strength of the inhomogeneous field;
subjecting the quantum sensor to the inhomogeneous field of the analyte;
subjecting a first qudit sensor of the quantum sensor to a first perturbation pulse;
receiving the first perturbation pulse by the first qudit sensor to prepare a first intermediate entangled state of the quantum sensor, the first intermediate entangled state comprising a first intermediate linear superposition;
changing the initial linear superposition to the first intermediate linear superposition in response to receiving the first perturbation pulse by the quantum sensor; and
determining a final entangled state of the quantum sensor after applying the first perturbation pulse to determine the modal amplitude of the inhomogeneous field of the analyte.

2. The process of claim 1, wherein qudits comprise a qubit, a qutrit, or a combination comprising at least one of the foregoing qudits.

3. The process of claim 1, wherein qudits comprise a neutral atom, an ion, a molecule, a solid-state defect, a superconducting circuit, or a combination comprising at least one of the foregoing qudits.

4. The process of claim 1, wherein the qudits comprise:
a first qutrit sensor; and
a second qutrit sensor,
wherein the initial entangled state is $$\frac{1}{\sqrt{2}}[|00\rangle + |11\rangle],$$

and
the final entangled state, after final evolution under coupling to the inhomogeneous field of the analyte, is $$\frac{1}{\sqrt{2}}[|00\rangle + e^{-it_f q}|21\rangle].$$

5. The process of claim 1, wherein the qudits comprise:
a first qubit sensor; and
a second qubit sensor;
a third qubit sensor;
wherein the initial entangled state is $$\frac{1}{\sqrt{2}}[|000\rangle + |111\rangle],$$

the intermediate entangled state comprises $$\frac{1}{\sqrt{2}}[|100\rangle + e^{-i\theta_2}|011\rangle],$$

and
the final entangled state, after final evolution under coupling to the inhomogeneous field of the analyte, comprises $$\frac{1}{\sqrt{2}}[|110\rangle + e^{-it_f q}|001\rangle].$$

6. The process of claim 1, wherein the modal amplitude q comprises a linear combination of a plurality of mode components $\alpha_i$ of a mode A and a plurality of energy components $\theta i$ as $$q = \sum_i^N \alpha_i \theta_i,$$

wherein N is a total number of qudits, and i is an integer from 1 to N.

7. The process of claim 1, wherein the first perturbation pulse comprises a termination pulse, an echo pulse, or a combination comprising at least one of the foregoing perturbation pulses.

8. The process of claim 1, further comprising:
subjecting a second qudit sensor of the quantum sensor to a second perturbation pulse;
receiving the second perturbation pulse by the second qudit sensor to prepare a second intermediate entangled state of the quantum sensor, the second intermediate entangled state comprising a second intermediate linear superposition;
changing the first intermediate linear superposition to the second intermediate linear superposition in response to receiving the second perturbation pulse by the quantum sensor; and
determining the final entangled state of the quantum sensor after applying the second perturbation pulse to determine the modal amplitude of the inhomogeneous field of the analyte.

9. The process of claim 1, wherein subjecting the first qudit sensor to the first perturbation pulse occurs at a time based on a smallest mode component of mode A.

10. The process of claim 1, wherein preparing the initial entangled state of the quantum sensor comprises subjecting the qudits to direct interaction among the qudits.

11. The process of claim 1, wherein preparing the initial entangled state of the quantum sensor comprises subjecting the qudits to a mediator comprising a photon, a phonon, or a combination comprising at least one of the foregoing mediators.

12. The process of claim 1, wherein the analyte comprises a planet, an organism, a tissue, a cell, a molecule, an atom, or a combination comprising at least one of the foregoing analytes.

13. The process of claim 1, wherein the inhomogeneous field comprises an electric field, a magnetic field, a temperature, a gravitational field, a strain, or a combination comprising at least one of the foregoing inhomogeneous films.

14. The process of claim 1, wherein determining the final entangled state of the quantum sensor after applying the first perturbation pulse comprises:
subjecting the quantum sensor to probe radiation; and
detecting whether the quantum sensor emits signal radiation in response to the probe radiation.

15. The process of claim 14, wherein the modal amplitude q is determined according to $$\left\langle \Psi \middle| \prod_{i=1}^N \sigma_i^x q \middle| \Psi \right\rangle = \cos(q t_f),$$

wherein $\Psi$ is a quantum state of the quantum sensor at a final time $t_f$ and $\sigma_i^x$ is a Pauli x operator acting on qubit i.

16. A computer-implemented method for determining a modal amplitude of an inhomogeneous field of an analyte, the method comprising:
preparing an initial entangled state of a quantum sensor, the initial entangled state comprising:
a first quantum level;
a second quantum level; and
an energy difference between the second quantum level and the first quantum level, the energy difference being linearly dependent on a strength of the inhomogeneous field,
the initial entangled state being an initial linear superposition of the first quantum level and the second quantum level, and
the quantum sensor comprising a plurality of qudit sensors;
subjecting the quantum sensor to the inhomogeneous field of the analyte;
subjecting a first qudit sensor of the quantum sensor to a first perturbation pulse;
receiving the first perturbation pulse by the first qudit sensor to prepare a first intermediate entangled state of the quantum sensor, the first intermediate entangled state comprising a first intermediate linear superposition;
changing the initial linear superposition to the first intermediate linear superposition in response to receiving the first perturbation pulse by the quantum sensor; and
determining a final entangled state of the quantum sensor after applying the first perturbation pulse to determine the modal amplitude of the inhomogeneous field of the analyte.

17. A system comprising:
one or more computers configured to perform operations, the operations for determining a modal amplitude of an inhomogeneous field of an analyte, comprising:
preparing an initial entangled state of a quantum sensor, the initial entangled state comprising:
a first quantum level;
a second quantum level; and
an energy difference between the second quantum level and the first quantum level, the energy difference being linearly dependent on a strength of the inhomogeneous field,
the initial entangled state being an initial linear superposition of the first quantum level and the second quantum level, and
the quantum sensor comprising a plurality of qudit sensors;
subjecting the quantum sensor to the inhomogeneous field of the analyte;
subjecting a first qudit sensor of the quantum sensor to a first perturbation pulse;
receiving the first perturbation pulse by the first qudit sensor to prepare a first intermediate entangled state of the quantum sensor, the first intermediate entangled state comprising a first intermediate linear superposition;
changing the initial linear superposition to the first intermediate linear superposition in response to receiving the first perturbation pulse by the quantum sensor; and
determining a final entangled state of the quantum sensor after applying the first perturbation pulse to determine the modal amplitude of the inhomogeneous field of the analyte.

18. A non-transitory computer-readable medium instructions stored thereon, which, when executed by a processor, cause the processor to perform operations for determining a modal amplitude of an inhomogeneous field of an analyte, the operations comprising:

preparing an initial entangled state of a quantum sensor, the initial entangled state comprising:
a first quantum level;
a second quantum level; and
an energy difference between the second quantum level and the first quantum level, the energy difference being linearly dependent on a strength of the inhomogeneous field,
the initial entangled state being an initial linear superposition of the first quantum level and the second quantum level, and
the quantum sensor comprising a plurality of qudit sensors;
subjecting the quantum sensor to the inhomogeneous field of the analyte;
subjecting a first qudit sensor of the quantum sensor to a first perturbation pulse;
receiving the first perturbation pulse by the first qudit sensor to prepare a first intermediate entangled state of the quantum sensor, the first intermediate entangled state comprising a first intermediate linear superposition;
changing the initial linear superposition to the first intermediate linear superposition in response to receiving the first perturbation pulse by the quantum sensor; and
determining a final entangled state of the quantum sensor after applying the first perturbation pulse to determine the modal amplitude of the inhomogeneous field of the analyte.

* * * * *